(12) United States Patent
Colyer

(10) Patent No.: US 7,939,265 B2
(45) Date of Patent: May 10, 2011

(54) AGENTS FOR AND METHOD OF QUANTIFYING BINDING

(75) Inventor: John Colyer, Leeds (GB)

(73) Assignee: Badrilla Limited (GB)

( * ) Notice: Subject to any disclaimer, the term of this patent is extended or adjusted under 35 U.S.C. 154(b) by 741 days.

(21) Appl. No.: 10/597,015

(22) PCT Filed: Jan. 6, 2005

(86) PCT No.: PCT/GB2005/000015
§ 371 (c)(1),
(2), (4) Date: Jul. 6, 2006

(87) PCT Pub. No.: WO2005/066630
PCT Pub. Date: Jul. 21, 2005

(65) Prior Publication Data
US 2007/0184450 A1     Aug. 9, 2007

(30) Foreign Application Priority Data

Jan. 6, 2004    (GB) .................................. 0400122.8

(51) Int. Cl.
*G01N 33/53* (2006.01)
(52) U.S. Cl. ............................ 435/7.1; 435/7.2; 436/518
(58) Field of Classification Search .................. None
See application file for complete search history.

(56) References Cited

U.S. PATENT DOCUMENTS

| 4,521,521 | A  | * | 6/1985  | Abbott et al. ................. 436/517 |
| 5,458,874 | A  | * | 10/1995 | Pereira et al. ................. 424/85.1 |
| 5,798,448 | A  | * | 8/1998  | Caras et al. ................. 530/387.1 |
| 2002/0107640 | A1 | * | 8/2002  | Ideker et al. .................... 702/19 |
| 2003/0059461 | A1 | * | 3/2003  | Backer et al. ................. 424/450 |
| 2003/0091975 | A1 | * | 5/2003  | Leyland-Jones .................. 435/4 |
| 2004/0137425 | A1 | * | 7/2004  | Upmeier et al. .................. 435/5 |

FOREIGN PATENT DOCUMENTS

| WO | WO 98/44350    | * | 12/1998 |
| WO | WO 01/64942 A1 |   | 9/2001  |
| WO | WO 2005/066630 A3 |   | 7/2005  |

OTHER PUBLICATIONS

Brette et al. "Biphasic effects of hyposmotic challenge on excitation-contraction coupling in rat ventricularmyocytes" *AJP-Heart* 279:1963-1971 (2000).
Brockwell et al. "The Effect of Core Destabilization on the Mechanical Resistance of I27" *Biophysical Journal* 83:458-472 (2002).
Chen et al. "Purification and Characterization of Prostate-Specific Antigen (PSA) Complexed to •₁-Antichymotrypsin: Potential Reference Material for International Standardization of PSA Immunoassays" *Clin. Chem.* 41(9) 1273-1282 (1995).
International Search Report for PCT/GB2005/000015; date of mailing Apr. 8, 2005.
Prestigiacomo et al. "A universal calibrator for prostate specific antigen (PSA)" *Scan J Clin Lab Invest* 55 Suppl 221 57-59 (1995).
Rodriguez et al. "Critical Evaluation of Cardiac CA2 +-ATPase Phosphorylation on Serine 38 Using a Phosphorylation Site-specific Antibody" *The Journal of Biological Chemistry* 279:17:17111-17119 (2004).
U.K. Search Report for Application No. GB400122.8; Mar. 29, 2004.

* cited by examiner

*Primary Examiner* — Jacob Cheu
(74) *Attorney, Agent, or Firm* — Myers Bigel Sibley & Sajovec, PA

(57) ABSTRACT

The present invention provides a presentation system and method of use for quantifying a target moiety in a sample which may contain the target moiety, the method comprising using a specified concentration or varying the concentration of a presentation system in order to generate a comparison point or calibration curve which provides means for comparing a signal generated by the presentation system and a signal generated by a sample, wherein said presentation system comprises at least one copy of said target moiety or part thereof.

25 Claims, 12 Drawing Sheets

Figure 4
Figure 4A
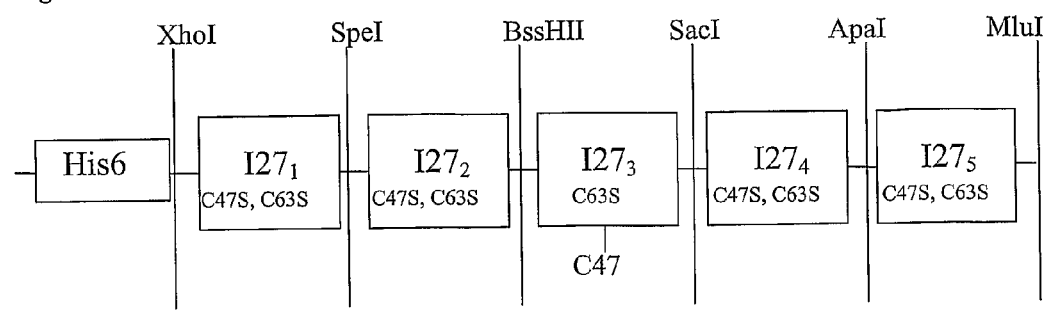
Figure 4B
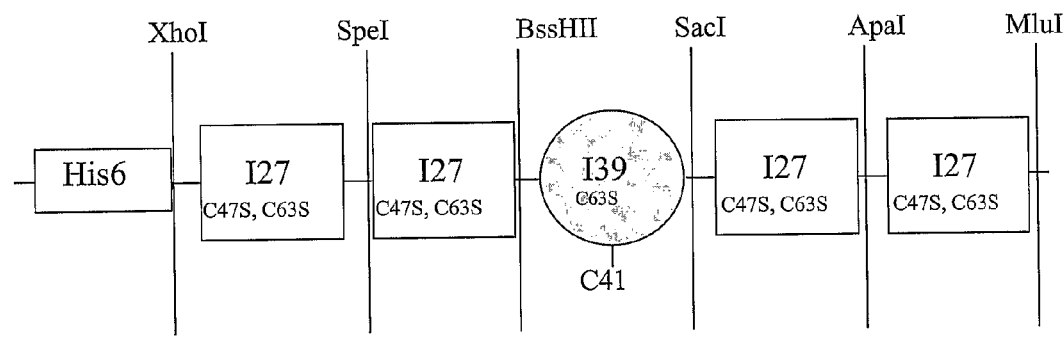

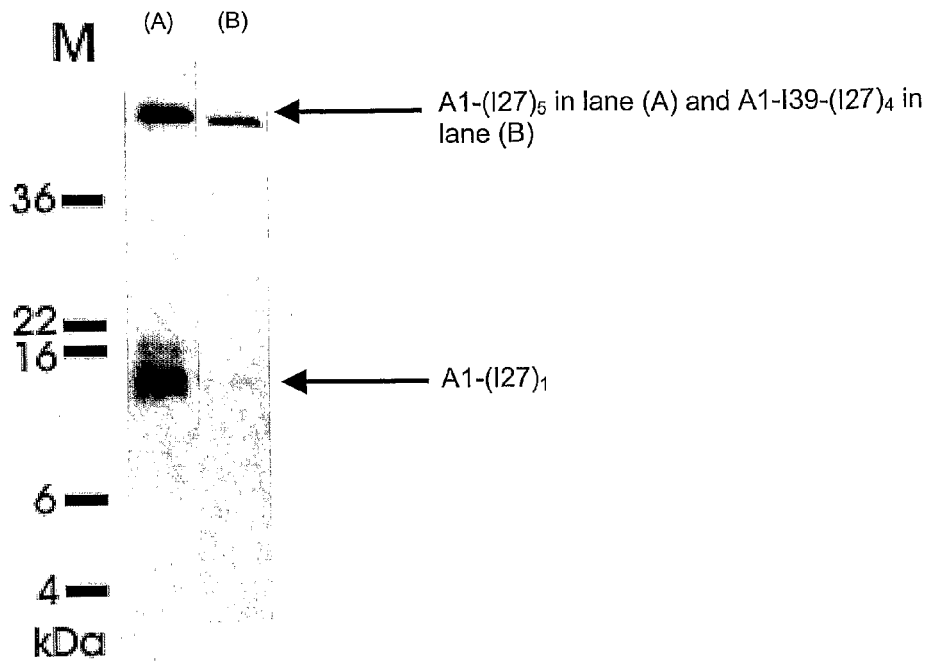
Figure 6
Figure 7A
Figure 7B
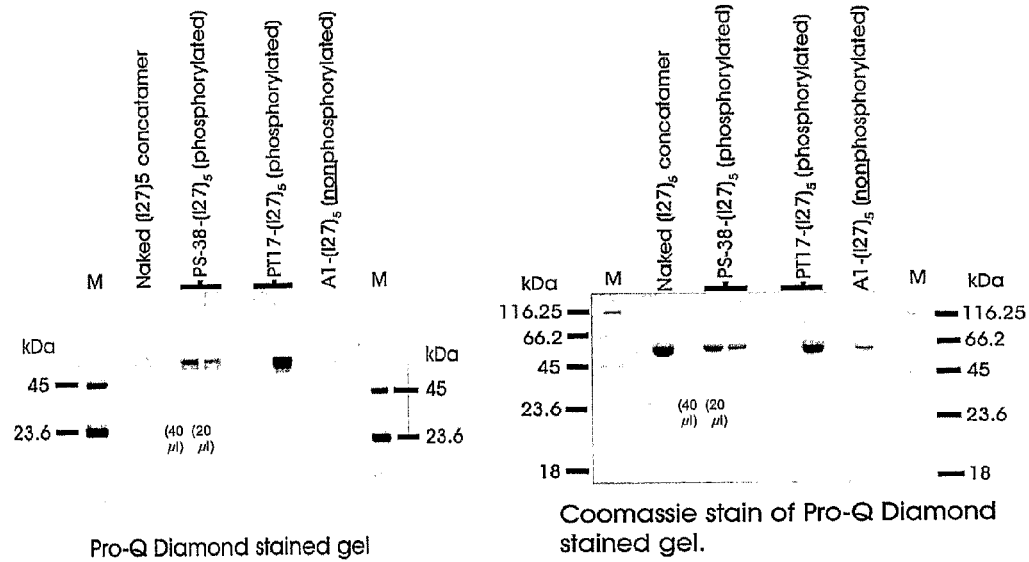
Pro-Q Diamond stained gel
Coomassie stain of Pro-Q Diamond stained gel.

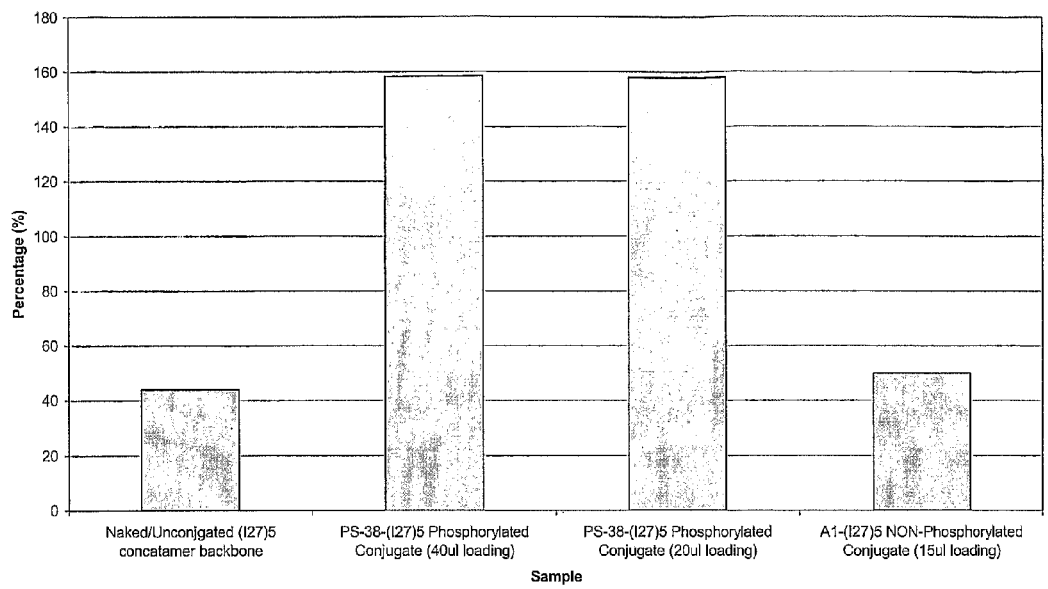
Figure 8
Figure 9
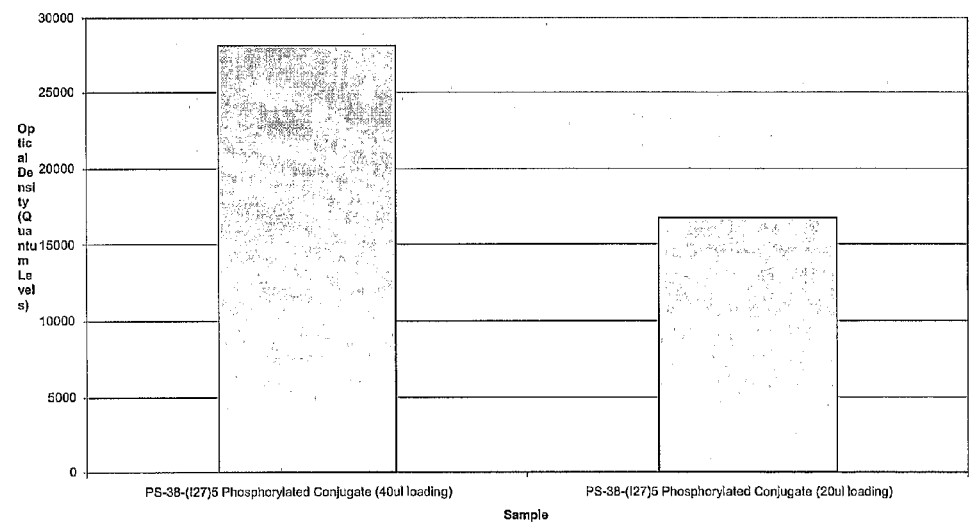

Figure 10
Figure 10A
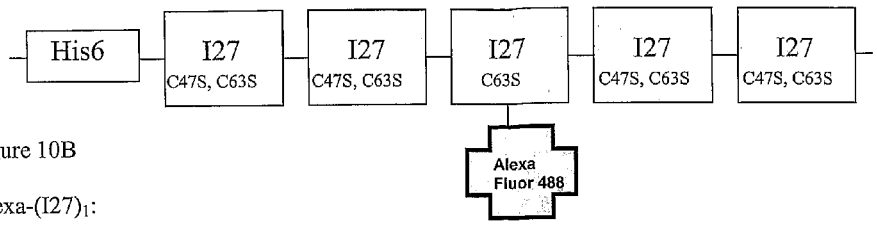
Figure 10B
Alexa-(I27)₁:
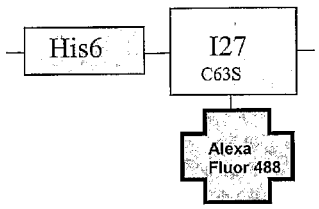
Figure 11
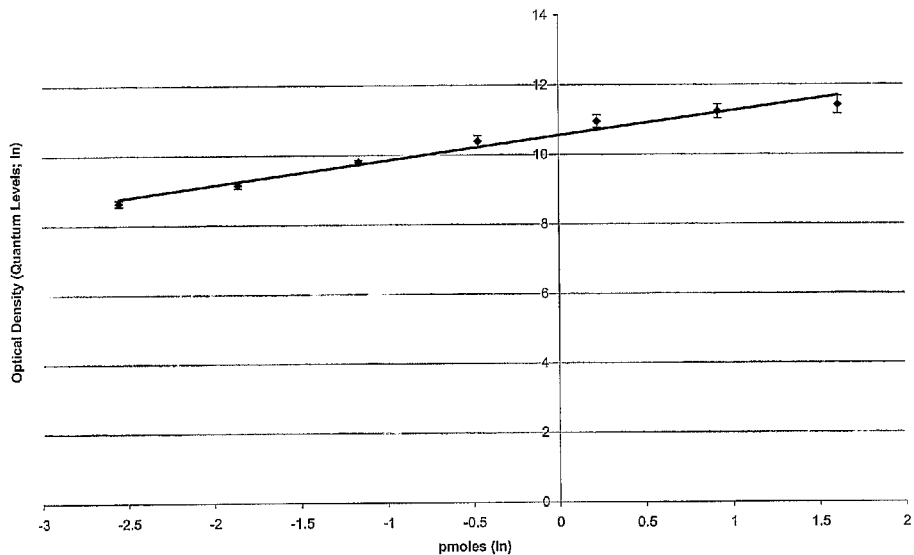

Room temp.

M
64—
50—
36—

22—
16— ← PT17-(I39)$_1$

6—
4—
kDa

Figure 17
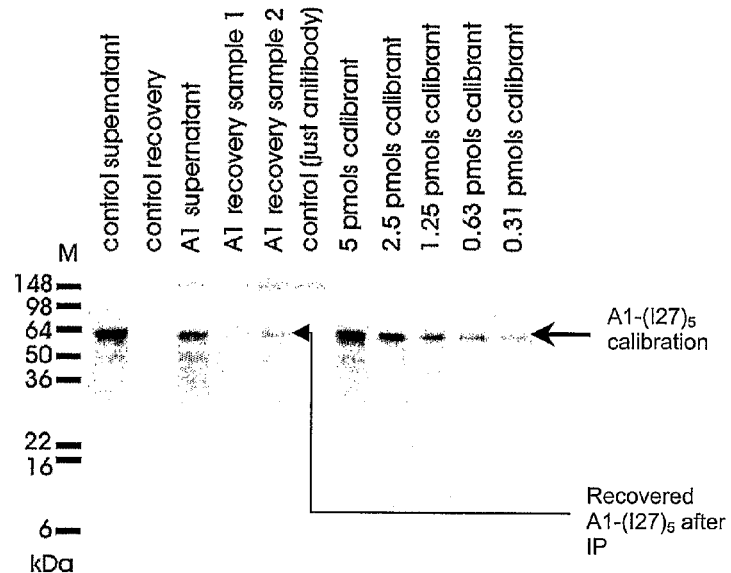
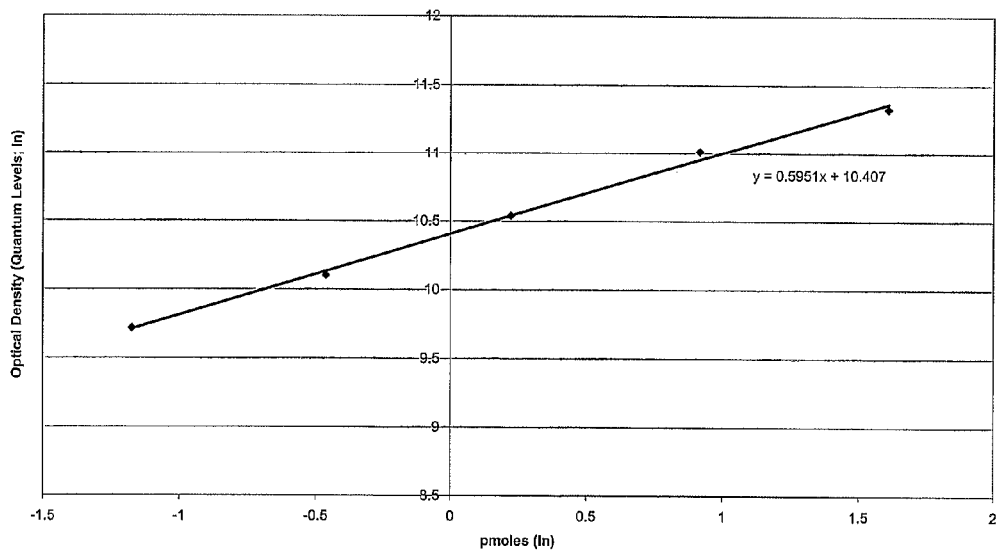
Figure 18

AGENTS FOR AND METHOD OF QUANTIFYING BINDING

RELATED APPLICATION

This application is a national phase application of PCT Application PCT/GB2005/000015, filed Jan. 6, 2005, and published in English on Jul. 21, 2005 as International Publication No. WO 2005/066630, which claims priority from British Application No. 0400122.8, filed Jan. 6, 2004. These disclosures are hereby incorporated by reference herein in their entireties.

FIELD OF INVENTION

The present invention relates to agents for and a method of quantifying binding of an agent to a specific binding partner, calibration products and uses thereof. The present invention, especially but not exclusively, is for use in blot based detection techniques and relates to quantification of the amount of an agent in a sample.

BACKGROUND TO THE INVENTION

Separation techniques such as blot-based techniques can be used to identify the presence of a particular target molecule in a sample. One blot-based technique, Western blotting, can be used to identify the presence of a particular protein in a sample through its interaction with an antibody specific for said protein. The proteins of a sample may be separated from each other by electrophoresis, transferred to a suitable membrane support, which is then interrogated with the specific antibody. The binding of antibody to the protein is visualised as a "spot" on the membrane, providing information as to its presence and location. The location may give information about the physical state of protein, for example glycosylation, phosphorylation or proteolysis.

A disadvantage of Western blotting and other immunological techniques is that the data generated are qualitative (unit-less), which limits the information obtained from an experiment and does not provide quantitative results comprising units. Furthermore, considerable day-to-day variation in sensitivity is observed, which prevents ready comparison between experiments performed on separate occasions, particularly when the experiments are performed by different researchers. Accordingly, there is considerable inter-experimental variation which makes comparisons between experiments difficult and inaccurate. These shortcomings limit both the quality of information gained and the productivity of the technique.

There are a variety of other blot based detection techniques. Southern blotting is a technique used to detect the presence of a particular DNA sequence, whilst Northern blotting is used to locate a particular RNA sequence within a mixture. ELISA techniques are highly sensitive, and therefore able to detect very small amounts of protein or other antigenic substance in a sample. The basis of this method is the binding of the antigen by an antibody that is linked to a surface of a plate. Formation of an immune complex is detected by use of peroxidase coupled to an antibody, the peroxidase being used to generate an amplifying colour reaction. However, despite the highly sensitive nature of ELISA, it does not quantify the amount of protein or antigen present in the sample. Thus, the disadvantages described in connection with Western blotting are also relevant to other blot based detection techniques.

There are other separation based techniques such as High Performance Liquid Chromatography (HPLC) and isoelectric focusing. Isoelectric focusing techniques are techniques used to separate proteins which utilise differences in the isoelectric points of the proteins. The isoelectric point of a protein is the pH at which a protein has no net charge. Under those circumstances it will not migrate in an electric field. Isoelectric focusing techniques use a pH gradient set up between a cathode and an anode and proteins will migrate towards their isoelectric point. Isoelectric focusing techniques do not provide truly quantitative results.

It is therefore long been desired that simple, effectively reproducible calibration technology would correct the described shortcomings and provide quantitative data which are readily comparable between experiments.

STATEMENTS OF INVENTION

The present invention resides in the covalent attachment of a target moiety to at least one or more controlled number of sites or domains in a scaffold material, the scaffold material having a controlled property. In this way the target moiety and scaffold material comprise a presentation system which can be used as a positive control, an internal standard or may be used to generate a calibration curve.

The present invention also provides a method of quantifying a target moiety in a sample which may contain the target moiety, the method comprising using a specified amount or varying the amount of a presentation system in order to generate a comparison point or calibration curve which provides means for comparing a signal generated by the presentation system and a signal generated by a sample, wherein said presentation system comprises at least one copy of said target moiety or part thereof.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entireties with respect to the text referenced by the citation.

According to a first aspect of the invention there is provided a presentation system for use in quantifying an amount of a target moiety which is present in a sample, the presentation system comprising at least one copy of a target moiety or part thereof that is recognisable by a binding partner and at least one domain of a scaffold covalently linked to said target moiety, said domain being non-reactive to a binding partner specific to said target moiety or part thereof.

Reference herein to target moiety or part thereof includes, but is not limited to sequences of DNA, RNA, protein or peptide, an antigenic structure or a chemical entity or moeity. The target moiety may further include saccharides, metabolite cofactors, haptens or modification groups. Modification groups may include phosphate, nitrosylated groups, sulphated groups or glycosylphosphatidyl inositol (GPI) groups.

Preferably the scaffold material of the presentation system has a controlled property, preferably this property is relative molecular mass (Mr) or weight (Mwt) or the pH value for the isoelectric point of a given substance in solution (pI).

Preferably, the scaffold material is a protein.

Preferably the scaffold material comprises at least one natural or unnatural amino acid with at least one or more chemically reactive groups, preferably within the side chain of a residue.

Preferably the scaffold comprises one or more chemically reactive groups, for example, the carbonyl on glutamic acid or aspartic acid or the hydroxyl on tyrosine and more preferably still comprises at least one cysteine and/or lysine amino acid groups. Thus it will be appreciated that the scaffold material may be a thiol or primary amine or any other protein in which there are suitable reactive side chain groups such as aspartic acid, glutamic acid, cysteine and/or lysine groups available for covalent conjugation with the target moiety. It is desirable that the covalent conjugation of the target moiety to the chemically reactive groups of the scaffold domains be controlled.

Preferably, the number of reactive cysteine and/or lysine groups may be controlled by selecting the scaffold protein from a natural source which contains the desired number of reactive cysteine and/or lysine groups.

Preferably, the scaffold protein is selected from the group comprising: I27, from titin which contains two cysteine residues; I39 domain which is a subunit (subunit 5) of splicing factor 3b and which contains one cysteine residue, organ of Corti protein (*Mus musculus*) Swiss-Prot/TrEMBL Primary Accession Number Q8R448 which contains one cysteine and one lysine residue; heat shock protein, mitochondrial (*Mus musculus*) Swiss-Prot/TrEMBL Primary Accession Number Q64433 which contains eleven lysine residues; splicing factor 3B subunit 5 (*Mus musculus*) Swiss-Prot/TrEMBL Primary Accession Number Q923D4 which contains one cysteine and five lysine residues; ubiquinol-cytochrome C reductase complex ubiquinone-binding protein QP-C (*Schizosaccharomyces pomme*) Swiss-Prot/TrEMBL Primary Accession Number P50523 which contains one cysteine and six lysine residues; E1B protein (Human adenovirus type 11) Swiss-Prot/TrEMBL Primary Accession Number Q8B8U6 which contains one cysteine residue; chaperonin (*Arabidopsis thaliana*) Swiss-Prot/TrEMBL Primary Accession Number P34893 which contains nine lysine residues; photosystem II reaction center H protein (*Arabidopsis thaliana*) Swiss-Prot/TrEMBL Primary Accession Number P56780 which contains three lysine residues; a NADH-ubiquinone oxidoreductase subunit, mitochondrial [Precursor] (*Homo sapiens*) Swiss-Prot/TrEMBL Primary Accession Number P56181 which contains one cysteine and nine lysine residues; signal recognition particle protein (*Mus musculus*) Swiss-Prot/TrEMBL Primary Accession Number P49962 which contains two cysteine and eight lysine residues; DNA polymerase delta subunit 4 (*Mus musculus*) Swiss-Prot/TrEMBL Primary Accession Number Q9CWP8 which contains two cysteine and six lysine residues.

Thus it will be appreciated that the presentation system of the present invention may provide a number of sites for covalent conjugation to a target moiety and that the scaffold may be selected according to a user's requirements. For example, the mitochondrial [Precursor] (*Homo sapiens*) Swiss-Prot/TrEMBL Primary Accession Number P56181 which contains one cysteine and nine lysine residues may be selected for attachment of a copy of the target moiety to the single cysteine residue or the organ of Corti protein (*Mus musculus*) Swiss-Prot/TrEMBL Primary Accession Number Q8R448 which contains one cysteine and one lysine residue may be selected for attachment of a copy of the target moiety either of the cysteine or lysine residues, in this respect the presentation system of the present invention is flexible to reducing to style reactive residues in the scaffold protein. A yet further means of tailoring the reactive residue sites is described herein after.

In a particular embodiment, the presentation system may comprise one or more domains, such as I27, from titin. Titin contains a number of β-sandwich domains belonging to the Ig family. The I27 domains usually contain two cysteine residues and fold to form stable structures of 10 kDa. In Nature, the I27 domain contains two cysteine residues (the site for covalent attachment of peptide), however mutation of these cysteine residues, to serine for example, is compatible with domain folding. Thus a presentation system of I27 can be formed where the molecular weight step size is a convenient unit (10 kDa steps) and where one unit (or more if required) can be engineered to possess a single cysteine residue for peptide attachment while all other units of I27 will lack cysteine residues. In alternative embodiments, the units of I27 may lack other reactive residues. These residues may include, but not be limited to lysine, glutamate and aspartate. A copy of I27 could contain one or more of these reactive residues, offering a controlled number of sites for the covalent attachment of target moieties.

Preferably, the number of reactive cysteine and/or lysine groups may be controlled by modifing any of the aforementioned scaffold proteins by selectively mutating by adding in or out or rendering ineffective any one or more of the reactive cysteine and/or lysine residues.

Alternatively, one or more of the titin domains may be mutated to possess either one or no cysteine residues. In one embodiment, the presentation system comprises one or more I27 domains and a copy of a target moiety, wherein one of the I27 domains comprises a single cysteine residue and the other I27 domains lack a cysteine residue. In a preferred embodiment, the presentation system comprises five I27 domains.

In an alternative embodiment, the domain(s) of the presentation system may comprise an I39 domain which is a subunit (subunit 5) of splicing factor 3b. The I39 domain is a 10 kDa domain.

As discussed previously, in one embodiment, the presentation system may comprise non-identical domains. For example, the presentation system may comprise at least one I39 domain and at least one I27 domain or any one or more of the aforementioned scaffold protein domains in addition to at least one copy of a target moiety or a part thereof. In an embodiment, the presentation system may comprise four I27 domains and one I39 domain or any other combination thereof including any one selected from the aforementioned domain from the scaffold proteins hereinbefore described.

Preferably, the domain or scaffold protein of the present invention is of a convenient molecular weight and is typically selected as 10 kDa for convenience.

Preferably, the presentation system may comprise a mixture of different types of units or domains or a number of identical domains. The units or domains may be of known molecular weight and/or pI and be blind to the binding partner specific to the target moiety or part thereof i.e. non-reactive thus, the units or domains of the presentation system may be considered capable of discrimination so that they are absolutely or relatively "immunologically blind" or "reactively inert" or substantially so. In a preferred embodiment, the at least one domain originates from a different molecule, or is a different species, to the target moiety or part thereof.

Reference herein to presentation system is intended to include, but not be limited to a molecule which comprises one or more linear units or domains which are linked in tandem.

In a further embodiment, the presentation system may comprise at least one biological or non-biological polymer. An example of a non-biological polymer is PEG (polyethylene glycols). In this embodiment, the presentation system may therefore be considered to be pegylated. In embodiments where the target moiety is a peptide or protein, the PEG polymer may be attached to functional groups of the at least one target moiety's amino acid sequence. Alternatively, the PEG polymer may be attached to sugar chains contained within the at least one copy of the target moiety in the presentation system.

The target moiety may be incorporated into the presentation system using a variety of known methods. For example, covalent attachment through a thiol group on a cysteine residue. In a particular embodiment, the target moiety may be conjugated to the presentation system. Alternatively, if the target moiety is a protein or peptide and the presentation system is also a protein or peptide, a DNA segment encoding the target moiety may be incorporated into the DNA encoding the presentation system, and subsequently expressed with the presentation system using known methods of protein expression.

In one embodiment, when the presentation system is a protein or peptide, it may comprise a number of stably folded protein domains. The number of domains may be varied in order to vary the molecular weight of the presentation system. In one preferred embodiment, at least one domain contains an amino acid capable of accepting a covalent bond from the target moiety or part thereof. In alternative embodiments, the at least one domain or the at least one copy of the target moiety or part thereof may be modified to provide for covalent attachment. The domains of the presentation system, apart from the target moiety or part thereof, are inert, that is to say, these domains are non-reactive to the specific binding partner of the target moiety or part thereof. The "inert" domains control the molecular weight of the presentation system to facilitate multiplexing of samples. Reference herein to multiplexing means the ready deconvolution of information derived from a procedure using a mixture of test and presentation system sample to obtain the signal derived from the test component and the signal derived from the presentation system.

What form the presentation system takes is dependent on the form of the target moiety to be detected and quantified. If, for example, the target moiety to be quantified is a nucleic acid, then the presentation system may comprise a sequence of nucleic acids. The presentation system may comprise a sequence of DNA units or domains of known molecular weight. Alternatively, the presentation system may comprise RNA units. Alternatively, if the target moiety is a peptide epitope or protein, then the presentation system will also comprise peptide units or domains, and Western blotting or ELISA can be used to quantify the amount of the target moiety present in the sample. It is also envisaged that heterocombinations may make up the presentation system i.e. the presentation system may comprise both peptide and nucleic acid.

The target moiety or part thereof may be a peptide or protein sequence. Alternatively, or in addition, the target moiety or part thereof may be an epitope or antigenic sequence. The position of the target moiety or part thereof within the linear sequence of the presentation system may vary. In one embodiment of the present invention, the presentation system may have one copy of the target moiety or part thereof present in its sequence. In an alternative embodiment, the presentation system may comprise more than one copy of the target moiety or part thereof. In a particular embodiment, the presentation system may comprise differing target moieties or parts thereof. For example, in one embodiment the presentation system may comprise a protein sequence and also a metal or dye. In an embodiment, one of the target moieties may be a His-tag and another target moiety may be a peptide epitope. In these embodiments, the target moiety or part thereof in the presentation system may not be the target moiety which may be present in the sample.

The target moiety or part thereof may be linear or branched within the presentation system. That is to say the target moiety may have a covalent attachment through a side chain of the scaffold material. Reference herein to "branched" means non-linear and that the polymer is formed by a covalent bond through a side chain rather than back-bone of the peptide chain or equivalent for nucleic acids (backbone formed by phosphodiester bonds between carbons 3 and 5 of the ribose/deoxyribose ring; covalent bonding of target moiety to other sites in nucleic acid equates herein to a branched structure).

Reference herein to protein or product is intended to include: protein complexes or fragments; enzymes; enzymatic products or conjugates; primary metabolites; hormones or antibodies.

When the presentation system and/or the target moiety is a protein or peptide, the isoelectric point (pI) may be controllable. This particular embodiment provides particular advantages when the separation technique used is 2-D electrophoresis.

In a particular embodiment of the present invention, the target moiety comprises the protein SERCA2a. The presentation system may comprise an epitope of SERCA2a. SERCA2a is the cardiac muscle isoform of the sarcoplasmic reticulum Ca2+-ATPase family. In a preferred embodiment, the epitope of SERCA2a comprises the amino acid sequence CLEPAILE.

In an alternative embodiment, the target moiety is the protein SERCA2a which has been phosphorylated on serine-38. Preferably, the presentation system comprises an epitope from this protein. Preferably, the epitope comprises the amino acid sequence $^{31}$KLKERWGS(PO$_4$)NEL$^{41}$ Reference herein to specific binding partner refers to any molecule which has a specific binding affinity for the copy of the target moiety and is capable of binding thereto.

Preferably, the binding partner is selected from the group comprising antibodies, RNA or DNA or peptide aptamers or other antibody equivalents, dyes, drugs and metal chelates. The binding partner may be the same species as the target moiety e.g. polypeptide to peptide binding or nucleic acid polymer to nucleic acid polymer. Alternatively, the specific binding partner may be a different species to the target moiety for example nucleic acid polymer binding to peptide/polypeptide; dye binding to peptide/polypeptide. Where the target moiety is an antibody it may be monoclonal, for example and without limitation A1 or anti-his6, where the target is a polyclonal antibody it may for example and without limitation be a PS-38, PT-17, CLEP or an anti-Alexa fluor antibody. If the binding partner is an antibody, it may specifically bind to a target moiety which comprises a peptide epitope or dye epitope. Where, the specific binding partner is a metal chelate it may for example and without limitation be nickel ions, in the form of a Ni+peroxidase.

In a specific embodiment of the present invention, the presentation system comprises at least one I27 domain and/or at least one I39 domain and a target moiety is selected from A1 (LTRSAIRRAS), PS-38 (already defined) or PT17 peptide (RSAIRRAST(P0$_4$)IEY).

Thus, the present invention further provides calibration standards which are simple and reliable and user-friendly and also enables the results of experiments carried out on separate occasions to be compared accurately.

In a further aspect of the present invention, there is provided a product for use in quantifying the amount of a target moiety which may be present in a sample, the product comprising a plurality of presentation systems, each presentation system comprising at least one copy of a target moiety or part thereof and at least one domain covalently linked to said target moiety, wherein the domain(s) is/are non-reactive to a binding partner specific to said target moiety or part thereof, further wherein each presentation system has a different molecular weight from other presentation systems in the product.

In a yet further aspect of the invention, there is provided a kit for quantifying the amount of a target moiety in a sample, the kit comprising a presentation system, said presentation system as hereinbefore described. Optionally, the kit further comprises a binding partner specific to the target moiety or part thereof. The domain(s) of the presentation system may be "inert" or blind to the binding partner, i.e. do not bind to the binding partner. Optionally, the kit may comprise instructions for use thereof.

In one embodiment of the invention, the presentation system is provided in a kit as a positive control sample. The kit further comprises an antibody product. The antibody product may be the binding partner. The presentation system comprises a target moiety or part thereof which will react with the antibody binding partner and thus provide a positive control.

In a yet further aspect of the invention there is provided the use of a product (presentation system) as hereinbefore described for quantifying the amount of a target moiety which may be present in a sample.

In a yet further aspect of the invention, there is provided a method of quantifying the amount of target moiety in a sample which may contain the target moiety, the method comprising:
a) providing a presentation system which comprises at least one copy of the target moiety or part thereof that is recognisable by a binding partner and at least one domain which is non-reactive to said binding partner, said at least one copy of the target moiety being covalently bonded to the at least one domain of a scaffold,
b) carrying out a separation detection technique on said presentation system, wherein said presentation system is present in a specific amount;
c) generating at least one comparison point comprising intensity of a signal produced by the presentation system versus the amount of the presentation system.

Preferably, the method includes any one or more of the features hereinbefore described.

Reference herein to separation based detection experiments or techniques can be taken to include, but not be limited to, detection techniques such as immunological assays based on detection by an antibody or other type of specific binding partner specifically recognising the target moiety, either when present in the presentation system or in a sample. Such assays include dot blots, Western blot, RIA, immunoprecipitation and fluorescence polarisation. Alternatively, the method of the present invention may utilise other blot based detections experiments or techniques such as Northern blotting or Southern blotting or PCR. Separation based techniques may also include High Performance Liquid Chromatography (HPLC), capilliary electrophoresis, mass spectrometry and isoelectric focusing and combinations of the above (e.g. 2D electrophoresis, HPLC-MS). It is envisaged that the method of the present invention may also be used in techniques such as ELISA. In alternative embodiments, mass spectrometry may be used as a detection method, either in isolation or in combination with other detection methods such as HPLC. The choice of technique will be dependent on the user's selection of binding partner and target moiety and is not intended to limit the scope of the invention. Appropriate choices of separation techniques are presented herein below and in the Examples.

Preferably, the method comprises a further step of comparing the comparison point or multiple comparison points with the sample to quantify the amount of target moiety present in the sample. Preferably, the presentation system is of a known molecular weight. Alternatively, or in addition, the presentation system is of a known pI. It is of particular advantage to have knowledge of the molecular weight of the presentation system in order to compare the presentation system with the sample which may contain the target moiety or part thereof. In one embodiment, the presentation system is present in a single amount. In this embodiment, a single comparative point will be generated. Thus, in this embodiment, the presentation system could be used as an internal standard. This could be used to confirm that detection of a target molecule has been performed correctly, wherein the presentation system operates as a positive control and a reference signal. This is particularly important in circumstances where the target molecule is absent from a sample (see example of FIG. 2).

Reference herein to the term "amount of the presentation system" may be considered to, in some embodiments, refer to the concentration(s) in which the presentation system(s) is/are used. In other embodiments, the term "amount of presentation system" may be considered to refer to the density in which the presentation system(s) is/are present in a sample. Density can be quantified using several methods, for example, detecting the fluorescent intensity of a sample or the light intensity.

It is envisaged that embodiments of the present invention may be used in the comparison of the protein repertoire of part or all of a cell or tissue is made between samples derived from different physiological states (e.g. states of development, disease vs. control etc.). It is now possible to stain for certain forms of post-translational modification of proteins, such as phosphoproteins and glycoproteins. The incorporation of an internal standard comprising a presentation system comprising a target moiety which is a suitably modified peptide structure (phosphopeptide, glycopeptide or other modified peptide) into the experimental design would improve quantitation of data and would permit the ready comparison of results between experiments run in parallel or on separate occasions.

Preferably, the presentation system is present in a series of varying amounts. In this embodiment, multiple comparison points may be generated and thus a calibration curve may be produced.

In one embodiment, the comparison point or calibration curve generated may then be used to quantify the amount of the target moiety in a sample. In particular, the comparison point or calibration curve generated by the present invention plots the intensity of the signal produced by the target moiety or part thereof as part of the presentation system against the concentration of the presentation system. A further separation based detection technique may then be carried out on a sample which may contain the target moiety. Alternatively, a further separation based technique may be carried out on a sample at the same time as the presentation system. The intensity of a signal, if any signal is observed, may then be determined. The comparison point may then be used to express the amount of target moiety in the sample relative to the amount of target in the calibration point, or calibration curve to determine the amount of target moiety present in the sample. The signal produced by the sample or presentation system may be, for example and without limitation, chemiluminescence. Other methods of detection include chromogenic substrates for enzyme catalysed detection, which are insoluble colour products, such as 4-methoxy-naphthol/$H_2O_2$ for peroxidase based anti-IgG, or fluorescence based detection systems which utilise fluorophores attached to a detecting reagent such as antibody or protein A or protein G. Radioactivity $^{125}$I labelled antibody or protein A or protein G. In an alternative embodiment, methods of detection involving the binding of dyes to the presentation system could be utilised. Dyes that could be used include, but are not limited to Pro-Q diamond (Molecular Probes, OR, USA), which is a dye for protein containing phosphorylated amino acids and Pro-Q emerald (Molecular Probes, OR, USA) which is a dye for carbohydrate containing moieties. Other binding partners could be other chemical molecules, such as a drug or candidate drug molecule.

In this embodiment, or other embodiments, the detection technique may include using INDIA™ HisProbe™-HRP chemistry. The Perbio™ INDIA HisProbe™-HRP probe is a nickel ($Ni^{2+}$)-activated derivative of horseradish peroxidase (HRP). The active ligand is a tridentate chelator that allows $Ni^{2+}$ to be bound in active form for subsequent interaction and detection of the target moieties. The active chelator has similar binding capacities to that reported for iminodiacetic acid, which has been long used for immobilized metal affinity chromatography (IMAC). Further detection techniques may be used in addition to INDIA™ HisProbe™-HRP chemistry, for example chemiluminescent substrate technology. Alternatively, other separation techniques may be used.

A separation technique, for example a blot based technique, may be carried out on the presentation system such that the presentation system migrates as a well focused or distinct band, which is separate from SERCA2a in the sample. The present method enables the user to unambiguously derive the presentation system from the sample, once the separation technique has been carried out. This is an example of multiplexing. Thus, the present invention provides a method which enables the generation of truly quantitative data from separation technique experimentation.

In one embodiment, more than one presentation system may be used to quantify the amount of a target moiety in a sample. In this embodiment, each presentation system may have a different molecular weight from the other presentation systems used. For example, presentation systems comprising only one domain may be placed in the same lane or channel as presentation systems containing two, three, four, five or more domains, thus providing a "ladder" of differing molecular weight presentation systems. Preferably, each of the presentation systems has a copy of the same target moiety or part thereof to facilitate comparison with a sample which may contain the target moiety.

In this embodiment, each presentation system may be in a differing concentration or amount to other presentation systems. Alternatively, the presentation systems may be in the same concentration or amount. One or more separation based detection techniques may be carried out on the plurality of presentation systems. The results of the separation based detection technique may then be used to create a calibration curve which may be used to determine the amount of target moiety present in the sample.

Thus, in one embodiment, the presentation system is present in one channel of a blot and a sample which may comprise the target moiety is present in a separate channel. In embodiments where a plurality of presentation systems of differing molecular weights are used, all of the presentation system samples may be loaded into a single channel, thus providing several reference points in a single lane. Similarly, in embodiments where samples containing a plurality of presentation systems which are present in differing concentrations are used, each sample containing a particular presentation system may be loaded into the same lane, thus providing an example of differing concentrations in a single lane. In such embodiments of the present invention, the method allows simultaneous examination of the presentation system and a sample which may contain a target moiety in a single experiment. This embodiment advantageously provides an unambiguous distinction between the presentation system and the sample, despite the separation based technique being carried out on both at the same time.

Alternatively, the presentation system and the sample may be present in the same channel or lane of the blot.

An embodiment provides a presentation system which comprises a target molecule or part thereof which is capable of binding to a drug molecule, which is the specific binding partner. The intensity of a signal produced by the presentation system may then be compared with the signal intensity of the sample.

In an alternative embodiment, the binding partner may be a stain or dye. One such stain is Pro-Q Emerald (Molecular Probes), which may be a binding partner when the target moiety or part thereof is a glycoprotein. A further example of a stain as a binding partner is Pro-Q Diamond (Molecular Probes), which may bind to a target moiety comprising a phosphoprotein. When the binding partner is a dye or stain, the domain(s) of the presentation system must be substantially "silent" and must not be strongly recognised or detected by the dye or stain.

Preferably, the binding partner is an aptamer. Aptamers are novel synthetic DNA or RNA ligands, which have been defined as artificial nucleic acid ligands that can be generated against amino acids, drugs, proteins and other molecules. Aptamers may be double-stranded DNA ligands or single stranded RNA ligands. They are isolated from complex libraries of synthetic nucleic acids by an iterative process of adsorption, recovery and reamplification (SELEX). RNA aptamers are nucleic acid molecules with affinities for specific target molecules. They have been likened to nucleic acid antibodies because of their ligand binding properties.

The presentation system may further comprise a tag or detectable molecule. The tag may carry out the function of purification of the presentation system. It will be appreciated that the position of the tag may be at the amino terminal or carboxy terminal or inserted internally with respect to the amino acid sequence of the presentation system. Other examples of tags or detectable molecules may include, but not be limited to, a polyHis-tag, FLAG, STREP, GST or a fluorescent label such as GFP. In an alternative embodiment, the tag may comprise the target moiety or part thereof of the presentation system.

In an alternative embodiment, immunoprecipitation may be used as a separation method. Immunoprecipitation is a technique that permits the purification of specific proteins for which an antibody has been raised. Thus, immunoprecipitation may be used to isolate the presentation system using an antibody to the target moiety or part thereof which makes up a portion of the presentation system and can also then be used to isolate the target moiety, if present, from a sample. Immunoprecipitation can be followed by SDS-PAGE and immunoblotting for analysis. In this embodiment, of the invention, derivatives of immunoprecipitation, affinity interactions which allow "pull-down" of a particular target material e.g. Ni-NTA beads to pull down (his)$_6$ tagged proteins, glutathione beads to pull down GST-tagged proteins can be used to monitor the efficacy of stages in the process.

The present invention delivers controlled, predictable manufacture of presentation systems. Furthermore, it will deliver calibration standards displaying the high quality characteristics including near homogeneous electrophoretic behaviour of presentation systems and multiplexing of test samples and presentation system samples. This has the advantage of increasing sample throughput.

In a yet further aspect of the invention there is provided a method for quantifying the amount of SERCA2a protein in a sample, the method comprising:
 a) providing a protein which comprises at least one copy of an epitope of SERCA2a that is recognisable by an antibody and at least one I27 domain from titin protein which is non-reactive to said antibody, wherein said protein is of a known molecular weight;
 b) carrying out a Western blot on said protein, wherein said protein is in a specific concentration;
 c) generating at least one comparison point comprising intensity of a signal produced by the protein versus the concentration of the protein.

Preferably, the protein is in a series of varying concentrations and the comparison point comprises a plurality of comparison points, thus providing a calibration curve. Preferably, the comparison point or calibration curve is then used to determine the amount of SERCA2a protein present in a sample by comparison of the intensity of signal produced by the sample with the calibration curve. In a preferred embodiment, the epitope comprises the amino acid sequence YLEPAILE.

In an alternative embodiment, the SERCA2a protein is phosphorylated on serine-38. Preferably, the protein comprises an epitope of the phosphorylated SERCA2a protein. In a particular embodiment, the epitope comprises the amino acid sequence $^{31}$KLKERWGS(PO$_4$)NEL.$^{41}$ In a yet further aspect of the invention, there is provided a method for quantifying an amount of a protein epitope in a sample, said method comprising:
 (a) providing a protein presentation system comprising at least one copy of the protein epitope and at least one further protein domain, wherein said presentation system is of known molecular weight;
 b) carrying out a Western blot experiment on said presentation system, wherein said presentation system is in a specific concentration; wherein said Western blot experiment utilises a binding partner specific to the target moiety; and further wherein said protein domain of the presentation system is non-reactive to the binding partner; and
 c) generating a comparison point comprising intensity of a signal produced by the presentation system in said technique versus the concentration of the presentation system.

Preferably, the presentation system is in a series of varying amounts and said comparison point is a plurality of comparison points which may be used to produce a calibration curve. In one embodiment, control of the number of target moieties within the presentation system can be achieved by selecting a protein with the desired number of reactive residues or by engineering the sequence of the protein such that it contains a limited number of acceptor sites for covalent attachment of the protein epitope. In a preferred embodiment there is only one site for covalent attachment. In alternative embodiments there may be more than one site for the protein epitope to attach to a protein domain to form a presentation system. An advantage of the present invention is that the molecular weight of the presentation system is controllable. This is achieved by employing a presentation system made up of a number of stably folded domains. In this embodiment, the domains are protein domains. By varying the number of domains in the presentation system, the molecular weight of the presentation system can be varied. In a preferred embodiment, one of these domains contains an amino acid capable of accepting a covalent bond from a modified epitope protein. The other domains are inert in this sense, but are present to control the molecular weight of the presentation system to facilitate multiplexing of samples and to facilitate the separation of multiple presentation system components, where multiple components exist (e.g. single shot applications as hereinafter described, internal standards for 2D electrophoresis).

The present invention advantageously enables accurate control of the molecular weight of the presentation system, across a wide Mr range (10 kDa-250 kDa or greater, or smaller if required). As a result, the present invention will deliver flexibility in the multiplexing of standards and test samples. It will also permit the development of an advanced format of the calibration standard technology, which allows the dispensing of the calibration standard range in a "single shot" thus maximising convenience for the end-user. In a preferred embodiment, a series of presentation systems, which may have differing molecular weights, are subject to a separation technique whilst loaded in a single channel. This embodiment provides the user with a variety of calibration standards to compare with samples if required. In a preferred embodiment, the method of the present invention utilises a plurality of presentation systems which may be used in a single experiment to provide a range. The plurality of presentation systems may be of differing molecular weight and may be mixed together or blended in specified molar ratios to achieve a range of presentation systems which may be used in a single separation based experiment or two detections can be made in the same presentation system.

The invention will now be described, by way of example only, with reference to the accompanying figures, in which:

FIG. 1: shows the specific recognition of a serine-38 presentation system (calibration standard). FIG. 1A shows a schematic representation of the calibration standard (referred to as calibration-38). Epitope peptide was covalently bonded to a cysteine residue in the third domain of an (I27)$_5$ concatamer as described in reference 9. FIG. 1B shows the calibration-38 composition described by electrospray mass spectroscopy. The product (calibration-38) is separated from substrate (I27)$_5$ components and a contaminant. Components marked with * were included in the calculation of product yield (5.4%). C) Calibration-38 (0.06-3.2 pmol) and calibration-αCLEP (0.3-60 pmol total (I27)5 protein) was analysed by Western blotting with antibody SERCA PS-38 (1:5000 dilution) following electrophoresis in 10% SDS-PAGE gels. SERCA PS-38 detected the calibration-38 product (~60 kDa) at loadings of 0.1 pmol and above. FIG. 1C shows that only calibration-38 is recognised by anti-SERCA-38 antibody, which confirms that the presentation system is immunologically silent.

FIG. 2 shows SERCA phosphorylation in rat cardiac myocytes is not detected by antibody SERCA PS-38. Thus, FIG. 2 is a negative result. Isolated rat ventricular myocytes were paced electrically at 0.5 Hz for 5 min unless otherwise stated. Cells (A; 10,000; B; 2,500; rod shaped cell count) were treated without further intervention (control lane 1) or with 1 µM isoproterenol (lane 2); exposed to increased stimulation frequency (2.5 Hz; lane 3); exposed to 2.5 mM extracellular calcium (lane 4); or exposed to 1 μM calyculin A (lane 5). A) Calibration-38 (concentration range 0.01 to 3.2 pmol) and rat myocytes were submitted to SDS-PAGE (10% polyacrylamide) and transferred to PVDF membrane. Blot was probed with antibody SERCA PS-38 (1:5000) and visualized with goat anti-rabbit IgG peroxidase together with an enhanced chemiluminescent substrate (SuperSignal West Femto Maximum Sensitivity Substrate, Pierce) B) In a parallel experiment, myocytes were separated by 15% SDS-PAGE and transferred to PVDF membrane. Threonine 17 phosphorylated phospholamban was detected using antibody PT-17 (1:5000).

FIG. 3: shows a SDS-PAGE gel carrying varying concentrations of a presentation system for SERCA2a protein in different lanes and a single lane containing a sample comprising SERCA2a protein. FIG. 3 shows an embodiment of the present invention being used as a positive control.

FIG. 4A: is a schematic representation of a $(I27)_5$ construct with five identical I27 domains. Domain 3 contains a free thiol group (C47) for the covalent attachment of a peptide with a thiol specific reactive group. FIG. 4A also shows the position of unique restriction sites in the corresponding gene.

FIG. 4B: is a schematic representation of $I39-(I27)_4$ construct with four identical I27 domains and a non-identical I39 domain, thus showing a presentation system comprising non-identical domains. The I39 domain contains a free thiol group (C41) for the covalent attachment of a peptide with a thiol specific reactive group. FIG. 4B also shows the position of unique restriction sites in the corresponding gene.

FIG. 5: shows the successful conjugation of 3 different peptides (PS-38, PT17 and A1) to the free thiol group on the identical and non-identical concatamers via their thiol specific malemide reactive group. $(A)=(I27)_5+PS-38/PT17$ or A1. $(B)=I39-(I27)_4+PS-38/PT17$ or A1. (M=markers, kDa=kiloDaltons). See Example 6

FIG. 6 is a Western blot showing that both $A1-(I27)_5$ and $A1-I39-(I27)_4$ can be blended successfully with $A1-(I27)_1$ in different ratios to give a 'ladder' display of the calibration standards. (A)=Blend between $A1-(M27)_5$ and $A1-(I27)_1$. (B)=Blend between $A1-I39-(I27)_4$ and $A1-(I27)_1$. Samples run on 15% SDS-PAGE gel. Conjugations and western blot were performed as previously described.

FIG. 7 shows a Pro-Q stained gel (FIG. 7A) showing the specific detection of phosphorylated conjugates and, on the right hand side (FIG. 7B), a Coomassie stained gel showing the total protein content of each sample. The markers are PeppermintStick phosphoprotein molecular weight standards (Molecular Probes), which also contain positive controls at 45 (Ovalbumin=phosphorylated) and 23.6 kDa (β-Casein=phosphorylated). $PS-38-(I27)_5$ was loaded at two different volumes of 40 and 20 μl respectively.

FIG. 8 is a Bar Chart showing optical density (measured using AIDA Image Analyser (Raytest)) of Pro-Q stained phosphoproteins expressed as a percentage of total protein Coomassie staining. FIG. 8 shows that the optical density for a phosphorylated conjugate is significantly increased over the inherent background fluorescence of naked unconjugated concatamer backbone and nonphosphorylated conjugates.

FIG. 9 is a Bar chart showing the proportional change in optical density as the sample volume is changed. By halving the sample volume of phosphorylated conjugate, the optical density of the sample is also reduced by approximately half. Therefore, the concatamer/conjugate can be used as a calibration standard for dyes.

FIG. 10A is a schematic representation of $Alexa-(I27)_5$ (see Example 7) and FIG. 10B is a schematic representation of $Alexa-(I27)^1$ (see Example 7).

FIG. 11 represents a calibration curve of $Alexa-(I27)_5$ conjugate (presentation system) (See Example 7).

Figure 12:
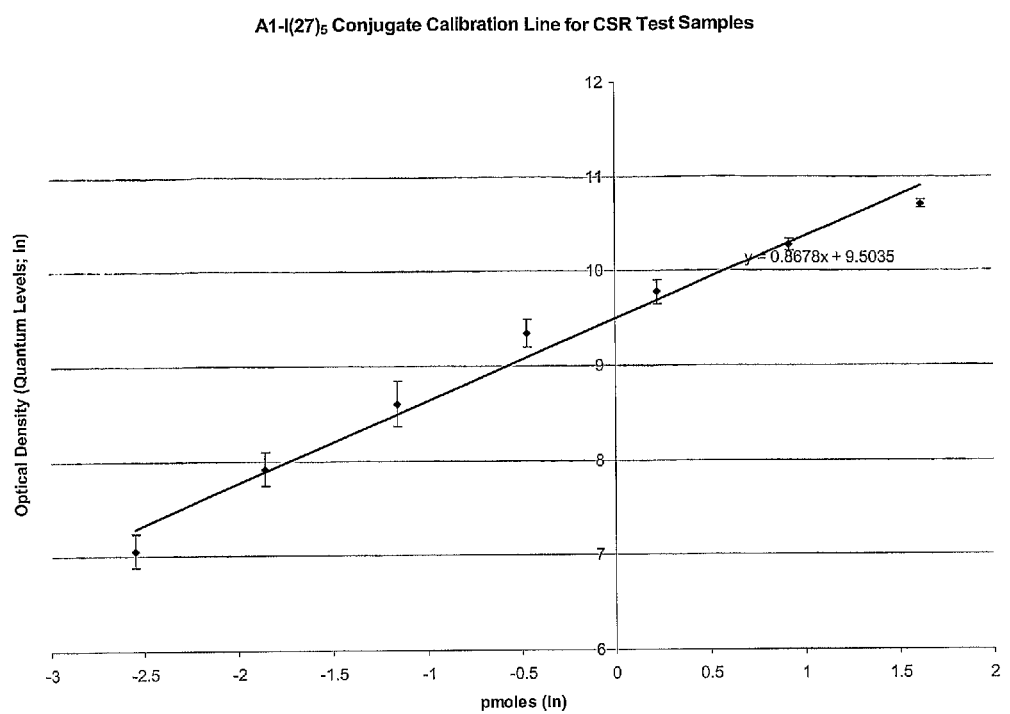

FIG. 12: Calibration curve of $A1-(I27)_5$ conjugate (presentation system).

Figure 13:
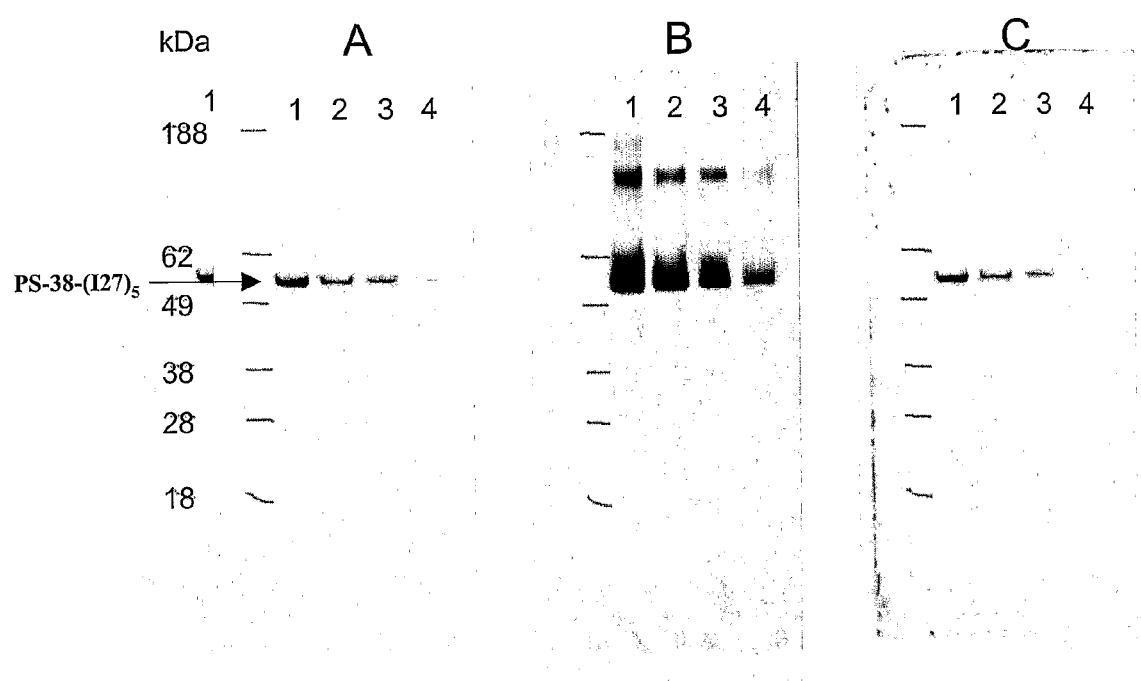

FIG. 13: demonstrates the detection of $PS-38-(I27)_5$ construct using two different detection methods and two different recognition epitopes.

Figure 14:
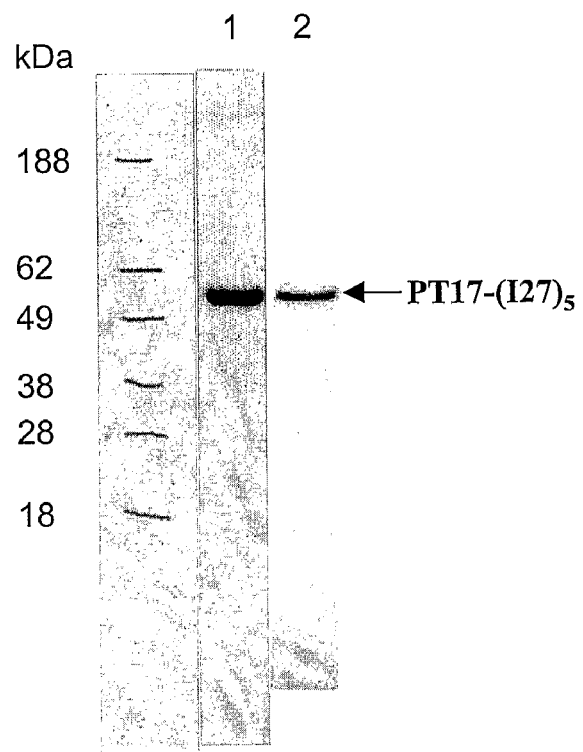

FIG. 14: Detection of the $PT17-(I27)_5$ construct using two distinct epitopes on the same molecule. Lane 1 represents detection of 5 pmols of $PT17-(I27)_5$ using a primary monoclonal antibody against the His6 tag epitope. Lane 2 represents the same blot which has been stripped and re-probed with an antibody raised to the PT17 peptide.

Figures 15, 16:
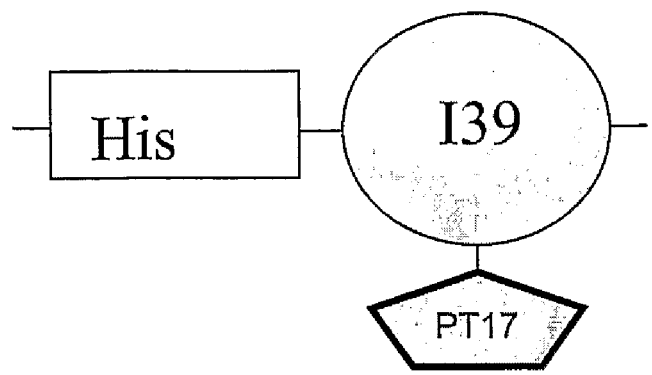

FIG. 15 shows conjugation of PT17 peptide to $(I39)_1$.

FIG. 16 is a Western blot showing conjugation of PT17 peptide to $(I39)_1$ at room temperature.

FIG. 17 shows immunoprecipitation of $A1-(I27)_5$ Conjugate.

FIG. 18 shows monitoring of efficiency of the IP experiment of FIG. 17.

DETAILED DESCRIPTION OF THE INVENTION

Construct A:—$(I27)_5$

With regard to the I27 domain of titin, the cysteine residue C47 is the site for covalent attachment of epitope peptide. (Refer to Example 2, section "Production of an Embodiment of the presentation system comprising a scaffolding protein comprising titin I27 domains (denoted $(I27)_5$ for details). A synthetic gene encoding five copies of I27 in series was constructed. Copies 1, 2, 4 & 5 of I27 lack cysteine residues, and copy 3 retains a single cys for peptide attachment. (His)6 module is included for product purification. Linker regions contain unique sequence & restriction sites (see FIG. 4A).

A construct comprising five I27 domains from the human titin molecule was inserted downstream of the His6 tag of pET3d. Domains $I27_1$, $I27_2$, $I27_4$, $I27_5$, have had their cysteine residues removed with the following mutations C47S and C67S. Domain I273 has had the cysteine residue removed at position 63 (C63S) but retains the cysteine residue at position 47 (see FIG. 4A).

Construct was expressed in the BLR(DE3)pLysS cell line (Novagen), cells being harvested 4 h post induction with 1 mM IPTG. See FIG. 4A for a schematic representation of the $(I27)_5$ construct. The unique restriction sites used for construction are shown in FIG. 4A.

Construct B:—$I39(I27)_4$

The term "I39" is being used as the abbreviation for the IMAGE clone 3965951 which is the cDNA clone provided by the IMAGE consortium of the mouse splicing factor 3b, subunit 5 gene (Accession BC006603). The mouse splicing factor 3b, subunit 5 gene product is a 10 kDa protein that contains a single cysteine residue.

PCR was employed to amplify the I39 cDNA and to engineer the addition of flanking restriction enzyme recognition sites, BssHII (5-prime) and SacI (3-prime). Using these two restriction enzymes the central $I27_3$ domain of the $(I27)_5$ construct (FIG. 4A.) was replaced by the I39cDNA sequence, creating the $I39(I27)_4$ construct (FIG. 4B). FIG. 4B shows the unique restriction sites used for construction.

The $I39(I27)_4$ construct was expressed in the BLR(DE3) pLysS cell line (Novagen), cells being harvested 1 h post induction with 1 mM IPTG.

Construct C: —I39pET14b. The term "I39" is being used as the abbreviation for the IMAGE clone 3965951 which is the cDNA clone provided by the IMAGE consortium of the mouse splicing factor 3b, subunit 5 gene (Accession BC006603), as discussed above.

PCR was employed to amplify the I39 cDNA and to engineer the addition of flanking restriction enzyme recognition sites, BamHI (5-prime) and BlpI (3-prime). Using these two restriction enzymes the PCR product was cloned into reciprocal sites in the expression vector pET14b (Novagen). For construction purposes the C-terminal residue of the protein was altered, N111T. The I39pET14b construct was expressed in the Rosetta-gami B(DE3)pLysS cell line (Novagen), cells being harvested 4 h post induction with 1 mM IPTG.

Example 1

The method of the present invention was used to detect the protein SERCA2a in a sample. A presentation system (calibration standard) for antibody α-CLEPAILE, which recognises the C-terminus of SERCA2a, was constructed as described for calibration SERCA-PS38 by reacting 0.1 micromole peptide YLEPAILE (single letter codes) with 5 micromole sulfosuccinimidyl 4-(N-maleimidomethyl)-cyclohexane-1-carboxylate (sulfo-SMCC); purification of peptide-cross-link complex by gel filtration chromatography; and incubation of the peptide-cross-link product with $(I27)_5$ (0.02 micromoles) in the presence of 9M urea. Product was dialysed against water and the protein concentration determined using a BCA assay and mass spectrometry as detailed in Example 2 under the section "SERCA PS-38 recognition of a calibration standard (presentation system)".

Quantitation of SERCA in a Sample of Cardiac Muscle Sarcoplasmic Reticulum.

Figure 3:
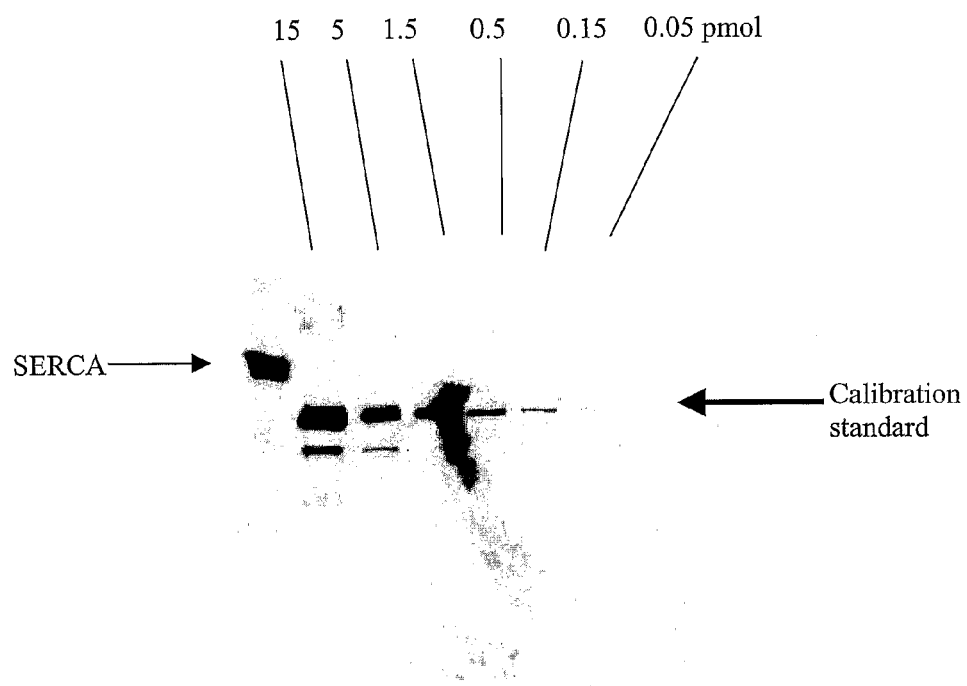

Cardiac sarcoplasmic reticulum (10 µg) and calibration-CLEPAILE standards (15-0.05 pmol) were separated in individual lanes on a 10% SDS-PAGE gel. The samples were transferred to PVDF membrane and probed with an antibody specific for the SERCA2a sequence LEPAILE (1:5000 dilution). Antibody binding to its epitope was detected using goat anti-rabbit IgG-peroxidase and a commercial chemiluminescent substrate preparation (Pierce). Chemiluminescence was detected using a CCD camera (FIG. 3).

Quantitation of the amount of SERCA2a in the sample can be achieved by analysis the band intensity of samples and calibration standards by densitometry. A plot of optical density (corrected for background signal) against quantity of the presentation system (calibration standard) should be prepared. This plot is considered to be a calibration standard curve. The SERCA2a protein content of the sample can be calculated using the calibration standard curve, by converting the optical density signal (corrected for background) of that sample to pmoles of epitope from this plot.

The above Example shows a way in which the presentation system and the method of the present invention may be used to positively identify a target moiety in a sample and to quantify the amount of target moiety in a sample.

Example 2

Example 2 shows a way in which the presentation system and the present method may be used to negatively identify a target moiety in a sample i.e. wherein the target moiety is not present in the sample.

The method of the present invention was used to detect phosphorylation of sacroplasmic reticulum Ca2+-ATPase SERCA2a) on serine-38. A standard Western blot approach had failed to detect serine-38 phosphorylated Ca2+-ATPase in either kinase treated sarcoplasmic reticulum vesicles and isolated rat ventricular myocytes.

The phosphorylation of the cardiac muscle isoform of the sarcoplasmic reticulum Ca2+-ATPase (SERCA2a) on serine-38 has been described as a regulatory event capable of very significant enhancement of enzyme activity. Independent confirmation of these observations has not been forthcoming. A polyclonal antibody, wholly specific for the phosphorylated serine-38 epitope on the Ca2+-ATPase, was utilised to evaluate the phosphorylation of SERCA2a in isolated sarcoplasmic reticulum vesicles and isolated rat ventricular myocytes. A quantitative Western blot approach failed to detect serine-38 phosphorylated Ca2+-ATPase in either kinase treated sarcoplasmic reticulum vesicles, or suitably stimulated cardiac myocytes. The presentation system of the present invention confirmed that the detection sensitivity of assays (0.03-0.1 pmol) was adequate to detect phosphorylation of just 1% of Ca2+-ATPase molecules on serine-38. Although a phosphoprotein of 100 kDa was evident in rabbit cardiac SR preparations, it was not recognised by the phospho-serine-38 specific antibody (2).

Preparation of Phospho-specific Antibodies.

Phosphorylated $Ca^{2+}$-ATPase peptide on Ser-38 residue ($^{31}$KLKERWGS(PO4)NEL$^{41}$) was prepared by the CaMKII phosphorylation of peptide $^{31}$KLKERWGSNEL$^{41}$. The phosphopeptide was purified to homogeneity by reverse phase high performance liquid chromatography. Peptide was conjugated to keyhole limpet haemocyanin (KLH) using carbodiimide cross linkage (3) and dialysed extensively against buffer (50 mM Tris-HCl pH 7.2, 150 mM NaCl). Adult New Zealand White rabbits were immunised with ~150 µg KLH and attached peptide at 6 weeks intervals and immune serum collected 11 days after immunisations. Serum was prepared and stored at −70° C. A polyclonal antiserum is described herein: SERCA PS-38 raised to the phosphorylated peptide.

Production of an Embodiment of the Presentation System Comprising a Scaffolding Protein Comprising Titin I27 Domains (Denoted $(I27)^5$).

A gene encoding a concatamer of mutant forms of the I27 domain of titin was used. The construct differs from the one described in Brockwell et al. (4) in that the two C-terminal cysteine residues have been deleted. It is referred to as $(I27)s$ throughout this study. $(I27)_5$ was expressed and purified as described in Brockwell et al. (4).

Presentation System: an Embodiment Comprising Peptide Conjugated to a Concatamer Purified phosphorylated Ser-38 peptide ($^{31}$KLKERWGS (PO$_4$)NEL$^{41}$) (0.1 µmol) was mixed with an excess of sulfo-succinimidyl 4-(N-maleimidomethyl)-cyclohexane-1-carboxylate (sulfo-SMCC) cross-linker (5 µmol) in buffer containing 0.1M sodium phosphate, 0.15 M NaCl, pH 7.2. After 1 h of incubation at room temperature, the maleimide-activated peptide was purified by gel filtration chromatography using a Superdex Peptide HR 10/30 column (Pharmacia Biotech). The chromatography was performing using 0.1M sodium phosphate, 0.15 M NaCl, pH 7.2 and a flow rate of 0.25 ml/min. Fractions of interest were pooled and urea was added to the fractions to make a final urea concentration of 9M. $(I27)_5$ concatamer (0.1 µmol) was added to the mixture and incubated for 2 h at room temperature. The conjugate was dialysed extensively against water. Final product (the presentation system according to the present invention) was stored at −20° C. The same procedure was followed to conjugate SERCA2a peptide (YLEPAILE) to $(I27)_5$ concatamer to form an alternative presentation system. Protein concentration was determined by a BCA assay (5).

Immunoblot Analysis.

Myocardial proteins were separated by SDS-PAGE using 10% and 15% polyacrylamide gels as described by Laemmli (8). Following separation, proteins were transferred to PVDF membranes (Pall BioSupport, Portsmouth, UK) by semi-dry blotting, and nonspecific binding sites were blocked for 2-4 h at room temperature using 5% dried milk and Tris-buffered saline (pH 7.4), 0.1% Tween 20. Membranes were probed overnight at 4° C. with primary antibodies: PT-17 (1:5000) for the Thr-17 phosphorylated form of phospholamban (6); α-CLEP (1:5000) for SERCA2a (16); and SERCA PS-38 (1:5000) antiserum specific for the Ser-38 phosphorylated form of $Ca^{2+}$-ATPase. A secondary horseradish peroxidase-labeled antibody raised in rabbit (Goat Anti-Rabbit IgG (H+L); Jackson Immunochemicals; lot number 38179) or protein A peroxidase (Sigma) were used in combination with two enhanced chemiluminescent detection system (SuperSignal West Pico Chemiluminescent Substrate and SuperSignal West Femto Maximum Sensitivity Substrate, Pierce) to visualize the primary antibodies. Data were captured using a Fuji LAS-1000 Imaging System CCD Camera (AIDA software for analysis).

The phosphorylation of SERCA2 on Ser-38 has been described as a regulatory feature capable of very significant activation of Ca2+-ATPase activity. This site, although unique to SERCA2, is contained within a segment of the protein which is highly conserved between SERCA1 and SERCA2 particularly from residue 39 onwards. As such, the two proteins are likely to display comparable structures in this region. By analogy with SERCA1, for which two high resolution structures exist the Ser-38 site of phosphorylation on SERCA2 is predicted to be in a surface exposed, highly mobile segment of the protein. This segment remains solvent exposed in both conformational extremes of the enzyme (E1, E2;), which would make it accessible to the kinase and phosphatase in these states. These properties also lend themselves to antibody binding to the site, as it is surface exposed, and highly mobile. We have produced a phosphorylation-site specific antibody to this feature in an effort to define the incidence and role of Ser-38 phosphorylation in cardiac muscle. A polyclonal antibody was produced to the sequence $^{31}$KLK-ERWGS(PO4)NEL$^{41}$, phosphorylated, as shown, at Ser-38 This polyclonal antiserum, SERCA PS-38, was wholly specific for the phosphorylated peptide, as the phosphopeptide was a potent inhibitor of antibody binding to antigen (IC50 18 nM), whereas the equivalent dephosphorylated peptide was unable to interfere with antibody:antigen recognition.

SERCA PS-38 Recognition of a Calibration Standard (Presentation System):

Having confirmed that polyclonal antibody SERCA PS-38 was wholly specific for the phosphorylated Ser-38 epitope we examined the phosphorylation status of this residue in SERCA following exposure of cardiac SR vesicles to CaMKII. SERCA was not detected in these Western blot experiments. It was important to establish the basis of this negative result, to ensure that it was providing information about the incidence of Ser-38 phosphorylation, rather than recording a technical failing of the antibody or experiment. To this end, we constructed a presentation system comprising a target moiety, in this case, the phosphopeptide epitope, attached to an inert scaffold protein of known molecular weight. The scaffolding protein was chosen as it contained a single site for peptide attachment (FIG. 1A) thus providing a uniform structure for the presentation of epitope peptide, ideal for accurate quantitation.

Figure 1:
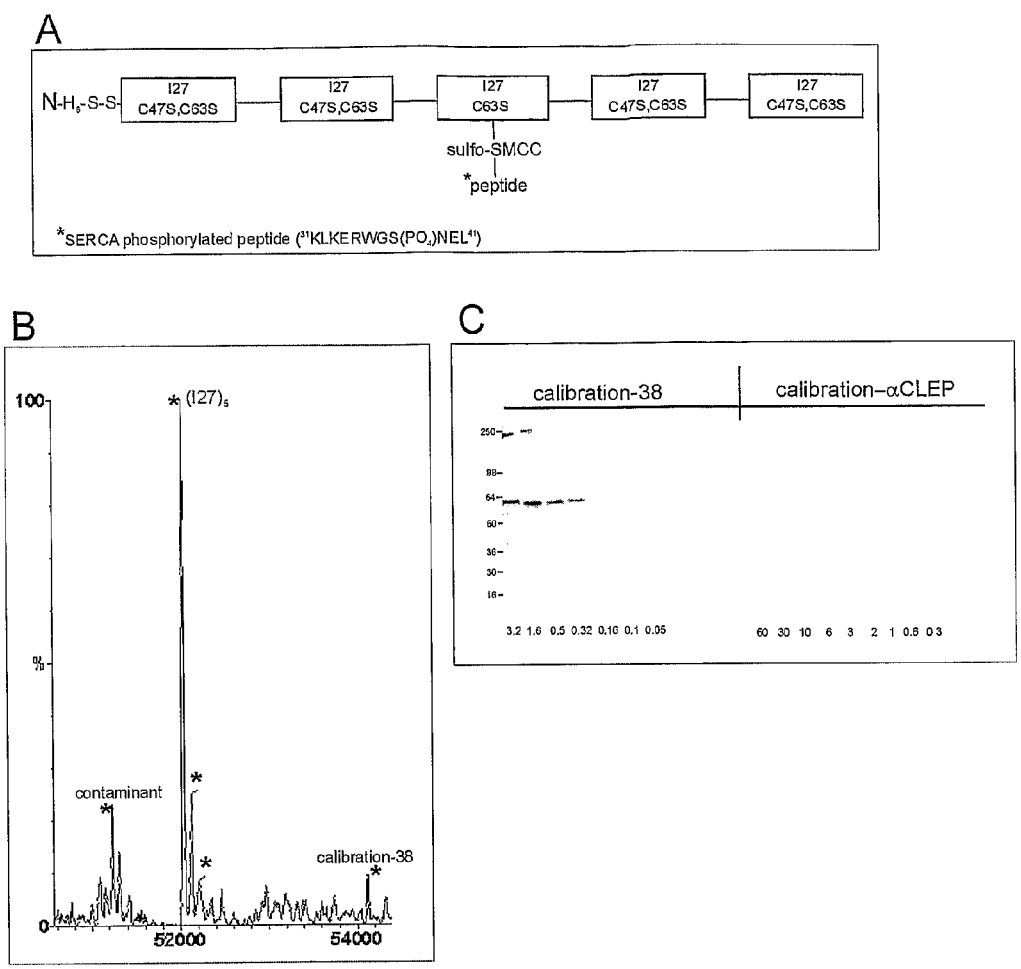
Figure 2:
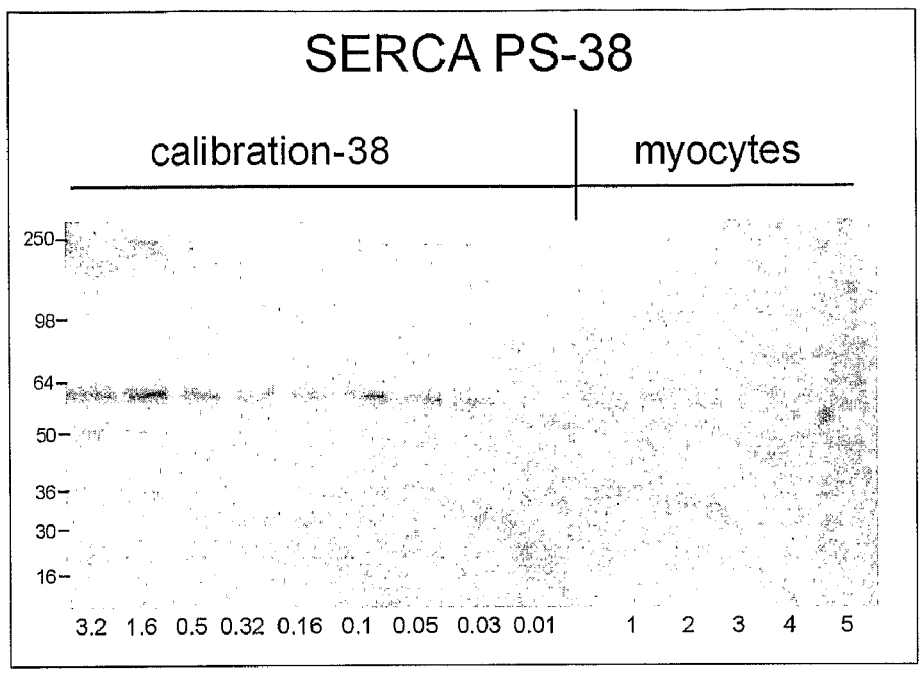
Figure 2:
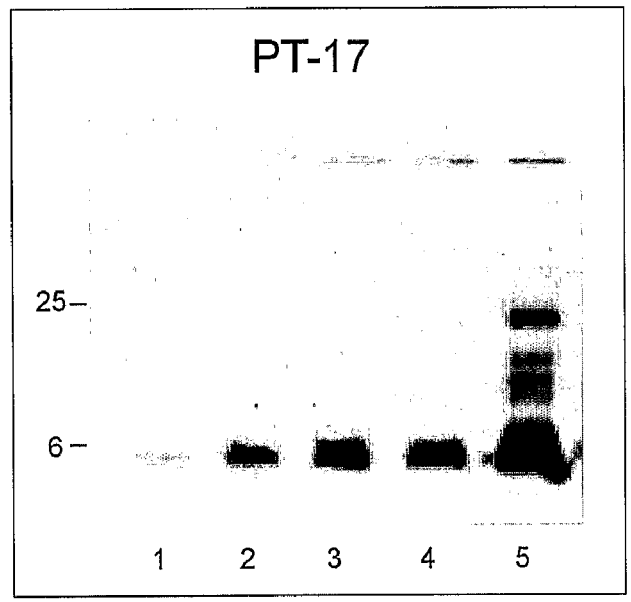

The presentation system employed comprised a concatamer of five copies of a domain from titin (I27), mutated to remove all but one cysteine residue from the concatamer sequence (FIG. 1A). The target moiety, in this case purified phosphoepitope peptide, was conjugated to the $(I27)_5$ concatamer via the only cysteine residue in the protein (C47 in I27 domain 3, presented schematically in FIG. 1A), and the stoichiometry of covalent attachment of the peptide was evaluated by mass spectrometry. A low stoichiometry of peptide attachment to the concatamer (final product mass 54124 Da, labelled calibration-38; FIG. 1B) was observed on this occasion, which comprises 5.4% of the total preparation. Nevertheless, this low level of conjugation to the concatamer proved sufficient for immunodetection (FIG. 1C). FIG. 1C shows that antibody SERCA PS-38 recognised the concatamer product decorated with the relevant phosphopeptide (calibration-38), but did not recognise the same concatamer $(I27)_5$ decorated with an irrelevant peptide (calibration-αCLEP) even when 60 pmol of concatamer was presented. The calibration standard migrates as a single molecular species of ~60 kDa in SDS-PAGE. Furthermore, the phosphorylated epitope was detected by antibody SERCA PS-38 with high sensitivity, down to a limit of 0.1 pmol epitope peptide using standard (SuperSignal West Pico, Pierce) ECL substrate (FIG. 1C).

The calibration standard (calibration-38) contained some minor contaminants. A contaminant of 51230 Da, seen on the mass spectrum, does not appear to accept peptide (not detected in Western blot experiments, FIG. 1C). This material was included in the calculation of percentage product (calibration-38) as it made an appreciable contribution to total protein. A second contaminant of the $(I27)_5$ preparation is covalently labelled by peptide. It underlies the immunostaining of a complex of high Mr (~250 kDa, FIG. 1C). This product was undetectable in the mass spectrum and therefore is present in low amounts in the calibration-38 preparation. It does not make an appreciable contribution to total protein and was excluded from consideration in the quantification performed in this study.

Thus we conclude that SERCA phosphorylation, if occurring at all, results in the generation of less than 0.03 pmol Ser-38 phosphoprotein in the cells studied (10,000 viable myocytes). In previous studies, Ser-16 phosphorylation of phospholamban in myocytes following similar interventions was quantified at 8.5 pmol/1,000 cells (7) indicating the presence of at least 85 pmol phospholamban in the 10,000 cells of the present study. As phospholamban and SERCA are expressed in similar amounts in cardiac muscle (2 phospholamban per SERCA, (1), we might expect 42 pmol of SERCA in the experiments performed. Our failure to detect Ser-38 phosphoprotein with the antibody described herein suggests that less than 0.1% of SERCA is phosphorylated in rat cardiac myocytes treated with CaMKII stimulants. The present study has described a polyclonal antibody wholly specific for a phosphorylated Ser-38 epitope on SERCA2. The antibody was able to detect the phosphorylated epitope in a calibration standard with high sensitivity (0.03-0.1 pmol). However, it failed to recognise SERCA2 in cardiac SR samples from a variety of animal species, despite the presentation of large amounts of SERCA (10-60 pmol) and the presence of a phosphoprotein of 100 kDa. This indicates that either SERCA is not phosphorylated on Ser-38, or that only a minor fraction of SERCA molecules (i.e less than ~1%) are phosphorylated on Ser-38. CaMKII activation in isolated cardiac myocytes was achieved using four independent stimuli resulting in phospholamban phosphorylation on Thr-17. None of these resulted in detectable Ser-38 phosphorylation of SERCA using this antibody, despite immunodetection of 0.03 pmol of the calibration standard in the same experiment. This indicates that between 0% and 0.1% of SERCA molecules become phosphorylated on Ser-38 in response to CaMKII activating stimuli in intact cardiac myocytes. This study does not provide evidence that Ser-38 phosphorylation of SERCA2a is a significant event in cardiac myocytes or cardiac SR preparations.

Example 3

Figure 5:
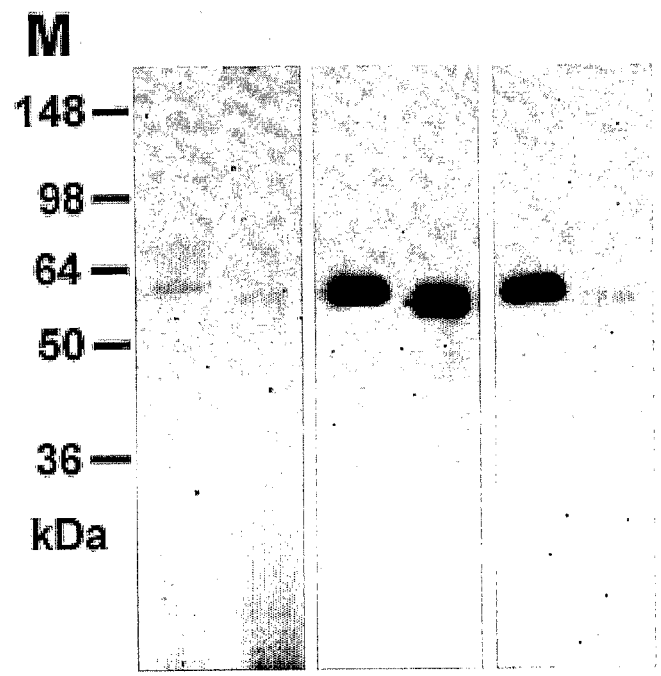

As shown in FIG. 5, three different peptides (PS-38, PT17 and A1) were conjugated to the free thiol group on the identical and non-identical constructs via their thiol specific maleimide reactive group. (A)=(I27)$_5$+PS-38, PT17 or A1. (B)=I39-(I27)$_4$+PS-38, PT17 or A1. (M=markers, kDa=kiloDaltons).

Conjugation reactions are performed by mixing a 1:100 molar ratio of concatamer (identical and non-identical) (dissolved in conjugation buffer containing 20 mM NaPO$_4$, 0.5 M NaCl and 8 M urea) to GMBS-modified peptide (dissolved in H$_2$O). GMBS is a heterobifunctional cross-linker. As used here, it contains a thiol directed reactive group. The amine reactive group of GMBS was used to attach the molecule to the N-terminus of the peptide during chemical synthesis of the peptide. The mixtures are left at room temperature for 2 hours.

Samples of each reaction are run out on a 12% SDS-PAGE gel and transferred overnight for western blot. Specific antibodies for each peptide are used to detect the conjugates:
  PS-38 primary antibody=Rabbit anti-PS-38 polyclonal (1 in 5000 dilution).
  PT17 primary antibody=Rabbit anti-PT17 polyclonal (1 in 5000 dilution).
  A1 primary antibody=Muse anti-A1 monoclonal (1 in 5000 dilution).

A secondary antibody is used to amplify the signal of the primary antibody. For a rabbit primary antibody, a goat-anti-rabbit HRP (horse radish peroxidase) secondary antibody is used (1 in 5000 dilution). For a mouse primary antibody, a goat-anti-mouse HRP secondary antibody is used (1 in 5000 dilution). Blots are imaged using Perbio SuperSignal West Pico Chemiluminescent kit (see above for reaction details).

Example 4

No Cross-Recognition of Conjugates with Irrelevant Antibodies

Samples of (I27)$_5$ and I39-(I27)$_4$ conjugated to either A1, PS-38 or PT17 peptide (as in example 3), and naked (unconjugated) concatamer backbone were put through a 12% SDS-PAGE gel in triplicate. The gel was then transferred to membrane, for western blot, overnight. The membrane is then split into three and probed with antibodies specific to an epitope on each peptide. Therefore, the antibodies should only recognise their specific epitope and not the epitope on a different peptide, or any part of the concatamer itself. We have generated a Western blot (data not shown) showing that each antibody recognises only its specific epitope on the peptide it was raised to and not the epitope of any other peptide. Also, the antibodies do not recognise and bind to the naked concatamer (presentation system without target moiety) itself.

Example 5

Blending of Different Sized Conjugates (Presentation Systems)

Conjugates of (I27)$_5$ and I39-(I27)$_4$ to the A1 peptide, and of (I27)$_1$ to the A1 peptide, produced as described in example 3 were blended together (A1-(I27)$_5$+A1-(I27)$_1$ and A1-I39-(I27)$_4$+A1-(I27)$_1$ separately) to show that a mixture of at least two different sized conjugates in the same sample can be run out, clearly separated and probed. This blend is not limited to conjugates based upon the same concatamer domain, but can work when one of the conjugates has a different functional domain (I39-(I27)$_4$). See FIG. 6.

Example 6

Staining of Calibration Standards/Conjugates with Phosphoprotein Specific Dye

See FIG. 7 and FIG. 8 for results. Samples of PS-38-(I27)$_5$, PT17-(I27)$_5$ and A1-(I27)$_5$ were run out on a 12% SDS-PAGE gel and stained with a phosphoprotein specific dye called Pro-Q Diamond (Molecular Probes). Only PS-38-(I27)$_5$ and PT17-(I27)$_5$ should be detected since only PS-38 and PT17 are phosphorylated. A1 is not phosphorylated, therefore, A1-(I27)$_5$ will not be detected. All samples and procedures were done in accordance with the dye manufacturer's instructions.

The markers used are PeppermintStick phosphoprotein molecular weight standards (Molecular Probes), which also contain positive controls at 45 (Ovalbumin=phosphorylated) and 23.6 kDa (β-Casein=phosphorylated). PS-38-(I27)$_5$ was loaded at two different volumes of 40 and 20 µl respectively.

The Pro-Q stained gel (left hand side of FIG. 7) shows the preferential detection of phosphorylated conjugates specifically from nonphosphorylated conjugates or proteins. This can be seen by the increased optical density of phosphorylated proteins over nonphosphorylated proteins, which do have some background fluorescence (also seen with non-phosphoprotein components of the PeppermintStick phosphoprotein Example 7

Complete Quantification of Conjugate and Production of Calibration Standard

Using a fluorophore (Alexa Fluor 488 (Molecular Probes)) it was possible to determine the exact amount of conjugate (presentation system) produced in a conjugation experiment. (I27)$_5$ and (I27)$_1$, were reacted with a 100 times molar excess of Alexa Fluor 488, which is thiol reactive, according to the manufacturers instructions. See FIG. 10. The conjugation mixture was dialysed against water to remove excess unbound fluorophore. The degree of conjugation was determined using a fluorimeter (to measure fluorescence emitted by the conjugate), spectrophotometer ($A_{280\ nm}$ to measure total protein content, $A_{493\ nm}$ to measure Alexa Fluor 488 content) and formulas provided by the manufacturer of the fluorophore (Molecular Probes). It was calculated that there was 100% conjugation between (I27)$_5$ and Alexa Fluor 488 (producing Alexa-(I27)$_5$), and 12% conjugation between (I27)$_1$ and Alexa Fluor 488 (producing Alexa-(I27)$_1$). Now the degree of labelling had been determined, an accurate and true calibration of conjugate could be produced.

A calibration curve of Alexa-(I27)$_5$ conjugate was loaded in triplicate on a 15% SDS-PAGE gel, transferred for western blot and then probed using an anti-Alexa Fluor (rabbit polyclonal IgG fraction) primary antibody (1 in 3000 dilution) and then a goat-anti-rabbit HRP secondary antibody (1 in 5000 dilution). The blot was then developed as previously described. Also loaded on the gel was three different blends of Alexa-(I27)$_5$ and Alexa-(I27)$_1$ showing that the blending capabilities of the conjugates is not influenced or determined by the entity bound to the concatamer. The Western blot (not shown) demonstrates that the moiety conjugated to the concatamer is not limited to peptides.

Seven different quantities of calibrant make up the calibration line: 5 pmols, 2.5 pmols, 1.25 pmols, 0.63 pmols, 0.31 pmols, 0.16 pmols and 0.08 pmols of Alexa-(I27)$_5$, loaded in triplicate. of Alexa-(I27)$_5$ and Alexa-(I27)$_1$ showing that the blending capabilities of the conjugates is not influenced or determined by the entity bound to the concatamer. The Western blot (not shown) demonstrates that the moiety conjugated to the concatamer is not limited to peptides.

Seven different quantities of calibrant make up the calibration line: 5 pmols, 2.5 pmols, 1.25 pmols, 0.63 pmols, 0.31 pmols, 0.16 pmols and 0.08 pmols of Alexa-(I27)$_5$, loaded in triplicate.

The optical density of each band, for each amount of Alexa-(I27)$_5$, was measured and like quantities were averaged and plotted in Excel to produce a calibration line (FIG. 12, mean+/− standard deviation). Such a calibration line can then be used to determine the previously unknown quantity of a sample.

Example 8

Using a Calibration Line of A1-(I27)$_5$ to Determine the Quantity of Phospholamban in Canine Sarcoplasmic Reticulum A calibration line of 5 pmols, 2.5 pmols, 1.25 pmols, 0.63 pmols, 0.31 pmols, 0.16 pmols and 0.08 pmols of A1-(I27)$_5$ was loaded in triplicate on a 15% SDS-PAGE, transferred for western blot and probed for the A1 epitope as previously described. The A1 epitope is from a protein called Phospholamban (PLB), which is present in the sarcoplasmic reticulum (SR) membrane. Three samples of canine sarcoplasmic reticulum (CSR) were also loaded on the gel/blot and the quantity of PLB in the samples was determined using the anti-A1 (mouse monoclonal) primary antibody, which recognises the A1 epitope of PLB in CSR (the same A1 epitope that is present on the A1 peptide used to produce A1-(I27)$_5$ conjugate).

Seven different quantities of calibrant make up the calibration line (FIG. 12): 5 pmols, 2.5 pmols, 1.25 pmols, 0.63 pmols, 0.31 pmols, 0.16 pmols and 0.08 pmols of A1-(I27)$_5$, loaded in triplicate. The optical density of each band, for each amount of A1-(I27)$_5$, was measured and like quantities were averaged and plotted in Excel (see FIG. 12, mean± standard deviation) to produce a calibration line. This calibration line can was used to determine the previously unknown quantity PLB in each CSR sample. Using the line in FIG. 12, the pmol quantity of PLB in each CSR sample was calculated.

Example 9

Detection of PS-38-(I27)$_5$ Construct Using Two Different Detection Methods and Two Different Recognition Epitopes With regard to FIG. 13, lanes 1 to 4 represent loadings of 20, 15, 10 and 5 pmols of PS-38-(I27)$_5$ conjugate. In Panel A, the blot was probed with the Perbio™ INDIA HisProbe™-HRP probe. Following stripping, the blot was re-probed with a polyclonal antibody specific to the PS-38 conjugated peptide, Panel B. The blot was stripped again and finally probed using a monoclonal antibody (Novagen) against the His-6 tag, Panel C.

Panel A of FIG. 13 shows the detection of the PS-38-(I27)$_5$ construct using the non-antibody mediated Perbio™ INDIA HisProbe™-HRP probe recognising the His6 tag epitope. Thus, the His-6 tag is considered one of the target moieties in this embodiment.

Panel B of FIG. 13 shows the detection of the PS-38-(I27)$_5$ construct using a primary antibody raised against the PS-38 peptide. (The additional band at approximately 150 kDa in Panel B is thought to be an oligomer of the construct, but could alternatively be a contaminant).

Panel C of FIG. 13 shows the detection of the PS-38-(I27)$_5$ conjugate using a primary antibody raised against the His6 tag. Thus, the primary antibody is considered a specific binding partner and the His6 tag is a target moiety.

Panels A, B and C indicate that the presentation system can be recognised by different detection methods and using different binding partners, i.e by modified enzymes (Panel A) and antibodies (Panels B and C). Furthermore, different target moieties on the same presentation system may be used for detection: His6 epitope (Panels A and C) and epitopes of the PS-38 peptide (Panel B).

Example 10

With regard to FIG. 15, there is shown an (I39)$_1$ domain that contains no I27 modules. Conjugation was done with a 100 molar excess of GMBS-PT17 to (I39)$_1$ at room temperature. Samples were run out on a 15% SDS-PAGE gel, transferred for Western blot and probed with anti-PT17 antibody as previously described. The blot shows detection of PT17-(I39)$_1$ after conjugation at room temperature.

Example 11

Immunoprecipitation of A1-(U27)$_1$ and A1-(I27)$_5$ Conjugates

A1-(I27)$_1$ conjugate was inmunoprecipitated with anit-A1 specific monoclonal antibody, using a standard protocol. By analysing the recovered sample by western blot (in different quantities) it is possible to determine the amount recovered using a calibration line of A1-(I27)$_1$. Immunoprecipitation was unsuccessful in this experiment, with 0% of A1-(I27)$_1$ recovered (data not shown). The A1-(I27)$_5$ conjugate was precipitated with anti-A1 specific monoclonal antibody, using a standard protocol. By analysis of recovered sample by Western blot (in different quantities) it is possible to determine the amount recovered using a calibration curve. FIG. 17 shows the Western blot of A1-(I27)$_5$ IP samples and A1-(I27)$_5$ calibrant. Seven different quantities of calibrant make up the calibration line: 5 pmols, 2.5 pmols, 1.25 pmols, 0.63 pmols and 0.31 pmols of A1-(I27)$_5$.

The optical density of each band for each amount of A1-(I27)$_5$ calibrant, was measured and plotted in Excel to produce the line of FIG. 18. This calibration line was used to determine recovered quantities of A1-(I27)$_5$ after IP. Using the graph, the pmol quantity of recovered A1-(I27)$_5$ after IP was calculated below.

A1-(I27)s was clearly immunoprecipitated (lane A1 recovery sample 2) whereas little was precipitated by Protein A beads alone (control recovery). Densitometry of the calibration curve samples and the immunoprecipitate samples permitted the calculation of 0.53 pmol A1-(I27)$_5$ in the immunoprecipitate. If 100% efficient, 30 pmol A1-(I27)$_5$ would have been recovered, therefore the process was 1.77% efficient.

The data also permit identification of where in the process inefficiency was introduced. Quantification of the samples control supernatant and A1 supernatant allowed description of A1-(I27)$_5$ material removed by the A1 antibody at the end of the immunoprecipitation process. This was 50 pmol of a possible 100 pmol, i.e. 50% efficient. The various wash steps post-immunoprecipitation were responsible for dramatic losses in product leading to a final yield (or efficiency) of 1.77%. This quantitative approach hereby allows description of the effectiveness of individual steps in an experimental (or industrial) process.

Thus it will be appreciated that in this example the presentation system and method of the invention may also be used to monitor efficiency of IP techniques during all stages so to assess at what point in the process is least/most effective and could benefit from improvements. It is also believed that the presentation system and method of the invention may also be used to monitor efficiency of other techniques.

References

1. Colyer, J., Wang, J. H. (1991) J Biol Chem. 266, 17486-93.
2. Goodfriend, T., Fasman, G., Levine, L. (1964) Science 144, 1344-1346.
3. Gopalakrishna, & Anderson (1982) Biochem. Biophys. Res. Comm. 104, 830-836
4. Brockwell, D. J., Beddard, G, S., Clarkson, J., Zinober, R. C., Blake, A. W., Trinick, J., Olmnsted, P. D., Smith, D. A., Radford, S. E. (2002) Biophys J. 83, 458-72.
5. Li, C, Wang, J. H., Colyer, J. (1990) Biochem. 29, 4535-4540.
6. Drago, G. A., Colyer, J. (1994) J. Biol. Chem 269, 25073-25077.
7. Brette, F., Calaghan, S. C., Lappin, S., White, E., Colyer, J., Le Guennec, J. Y. (2000) Am J Physiol Heart Circ Physiol. 279, H1963-71.
8. Laemmli, U. K. (1970) Nature Lond. 227, 680-685.
9. Rodriguez, P., Jackson, W. A., & Colyer, J. (2004) J. Biol. Chem. 279, 17111-17119

The invention claimed is:

1. A non-natural presentation system having a controlled molecular weight and isoelectric point, comprising at least one copy of a polypeptide target moiety or part thereof that is recognizable by a binding partner and at least one domain of a protein scaffold material covalently linked to said target moiety via a chemically reactive group in at least one side chain, wherein the protein scaffold material has a controllable property selected from the group consisting of:
   (i) number of chemically reactive cysteine amino acid residues; and
   (ii) number of chemically reactive lysine amino acid residues,
   wherein the domains of the scaffold are non-reactive to any detectable binding partner of the presentation system.

2. A method of quantifying the amount of target moiety or part thereof that is recognizable by a binding partner in a sample, the method comprising:
   a) providing a presentation system of claim 1;
   b) carrying out a separation detection technique on said presentation system, wherein said presentation system is present in a specific amount;
   c) generating at least one comparison point comprising an intensity of a signal produced by the presentation system versus the amount of the presentation system.

3. The method according to claim 2 wherein the presentation system is present in a single specific amount.

4. The method according to claim 2 wherein the presentation system is present in a series of varying amounts.

5. The method according to claim 4 wherein the varying amounts are in the same or different lanes or channels of a blot.

6. The method according to claim 4, wherein the comparison point is a plurality of comparison points which together provide a calibration curve.

7. The method according to claim 2 further comprising comparing the comparison point or comparison points with the sample to quantify the amount of target moiety present in the sample.

8. The method according to claim 2, wherein said presentation system is of a known molecular weight or pI.

9. The method according to claim 2, wherein the presentation system comprises a non-biological polymer, a nucleic acid molecule, a peptide, protein or combinations thereof.

10. The method according to claim 2, wherein the presentation system comprises a plurality of domains linked in tandem.

11. The method according to claim 2, wherein the presentation system comprises identical units or domains or non-identical or different units or domains.

12. The method according to claim 2, wherein the unit(s) of the presentation system is/are non-reactive to the binding partner specific to the target moiety of part thereof.

13. The method according to claim 2, wherein the copy of the target moiety or part thereof comprises sequences of DNA, RNA, protein or peptide, saccharides, haptens, phosphate, nitrosylated groups, sulphated groups, GPI groups, an epitope, an antigenic structure or a chemical entity.

14. The method according to claim 13, wherein the copy of the target moiety comprises SERCA2a or SERCA2a phosphorylated on serine-38.

15. The method according to claim 2, wherein the presentation system comprises differing target moieties or parts thereof.

16. The method according to claim 2, wherein the copy of the target moiety or part thereof is linear or branched within the presentation system.

17. The method according to claim 2, wherein the specific binding partner comprises a molecule which has a specific binding affinity for the target moiety and is capable of binding thereto.

18. The method according to claim 17, wherein the binding partner comprises an antibody, DNA sequence, RNA sequence, a polypeptide, a dye, a metal chelate or a drug molecule.

19. The method according to claim 2, wherein the separation based detection technique comprises a dot blot, Western blot, RIA, fluorescence polarization, ELISA, Northern blotting, Southern blotting, PCR, High Performance Liquid Chromatography (HPLC), capillary electrophoresis, 1D electrophoresis, isoelectric focusing, mass spectrometry or combinations of the above.

20. The method according to claim 2, wherein the presentation system is a positive control for detecting the presence or absence of a target moiety in a sample.

21. The method according to claim 2, wherein the presentation system is an internal standard by providing a one point calibration.

22. The method according to claim 2, wherein the presentation system is used to generate multiple comparison points so as to provide a calibration curve.

23. The method according to claim 2, wherein the presentation system is used to monitor efficiency of immunoprecipitation and/or stages of an immunoprecipitation process.

24. A method for quantifying an amount of a protein epitope in a sample, said method comprising:
(a) providing a protein presentation system of claim 1;
b) carrying out a Western blot experiment on said presentation system, wherein said presentation system is in a specific concentration; wherein said Western blot experiment utilizes a binding partner specific to the target moiety; and further wherein said protein domain of the presentation system is non-reactive to the binding partner; and c) generating a comparison point comprising an intensity of a signal produced by the presentation system in said technique compared to the concentration of the presentation system.

25. A kit for quantifying the amount of a polypeptide target moiety in a sample, the kit comprising a presentation system of claim 1.

* * * * *